(12) United States Patent
Clark et al.

(10) Patent No.: US 6,341,629 B1
(45) Date of Patent: Jan. 29, 2002

(54) TESTING DEVICE AND METHOD OF USE

(75) Inventors: Alisdair Quentin Clark, Hants; Harry Read, Surrey, both of (GB)

(73) Assignee: BP Oil International Limited, London (GB)

( * ) Notice: Subject to any disclaimer, the term of this patent is extended or adjusted under 35 U.S.C. 154(b) by 0 days.

(21) Appl. No.: 09/301,606

(22) Filed: Apr. 29, 1999

Related U.S. Application Data

(63) Continuation of application No. PCT/GB97/02951, filed on Oct. 28, 1997.

(30) Foreign Application Priority Data

| | | |
|---|---|---|
| Nov. 1, 1996 | (GB) | 9622840 |
| Mar. 6, 1997 | (GB) | 9704654 |
| Jul. 8, 1997 | (GB) | 9714270 |

(51) Int. Cl.[7] ............................................. B67D 5/372
(52) U.S. Cl. ................... 141/83; 141/1; 141/59
(58) Field of Search ............................ 141/1, 59, 83, 141/192, 290

(56) References Cited

U.S. PATENT DOCUMENTS

| | | |
|---|---|---|
| 3,926,271 A | 12/1975 | Pataschnick |
| 4,005,412 A | 1/1977 | Leander |
| 4,561,286 A | 12/1985 | Sekler et al. |
| 4,838,323 A * | 6/1989 | Watts .......................... 141/1 |
| 5,131,441 A * | 7/1992 | Simpson et al. ............ 141/209 |
| 5,172,738 A | 12/1992 | Komukai et al. |
| 5,201,215 A | 4/1993 | Granstaff et al. |
| 5,209,275 A * | 5/1993 | Akiba et al. .................. 141/83 |
| 5,225,679 A | 7/1993 | Clarke et al. ................ 250/343 |
| 5,309,957 A * | 5/1994 | Saisuu ......................... 141/83 |
| 5,330,073 A | 7/1994 | Collins et al. ................ 222/52 |
| 5,343,906 A | 9/1994 | Tibbals ........................ 141/83 |
| 5,782,275 A | 7/1998 | Hartsell, Jr. et al. |
| 5,934,507 A | 8/1999 | Motosugi |
| 5,975,165 A * | 11/1999 | Motosugi et al. ............. 141/83 |

FOREIGN PATENT DOCUMENTS

| | | |
|---|---|---|
| AU | B-21858/88 | 3/1989 |
| EP | 0 258 935 A1 | 3/1988 |
| EP | 0 440 299 A1 | 8/1991 |
| EP | 0 440 299 | 8/1991 |
| EP | 0 456 425 A1 | 11/1991 |
| EP | 0 476 858 A1 | 3/1992 |
| EP | 0 518 662 A2 | 12/1992 |
| EP | 0 566 345 A1 | 10/1993 |
| EP | 0 598 341 A1 | 5/1994 |
| EP | 0 802 157 A1 | 10/1997 |
| FR | 2 600 318 | 12/1987 |
| JP | 8-169498 | 7/1996 |
| WO | 95/19563 | 7/1995 |
| WO | 96/150064 | 5/1996 |
| WO | 96/29594 | 9/1996 |
| WO | 96/42011 | 12/1996 |

OTHER PUBLICATIONS

Abstract No. 88–065755/10, "Tanker loading and unloading checking method. . . ".
Abstract No. 91–232014/32, "Electronic data communication system between fluid reservoirs . . . ".

(List continued on next page.)

Primary Examiner—J. Casimer Jacyna
(74) Attorney, Agent, or Firm—Nixon & Vanderhye

(57) ABSTRACT

Method for controlling movement of a liquid from a first location to a second location via a dispenser for the liquid located in a liquid line between the first and second location. The dispenser includes a nozzle, an internal liquid conduit, a valve, a body portion, a hollow annular collar and a first detector. The first detector is located in the collar which is positioned around the nozzle or between the nozzle and the body portion such that the first detector is in vapor communication with a vapor space above the second location. The vapor from the vapor space is analyzed by withdrawing the vapor past the first detector and using the results of the analysis to control the operation of the valve.

24 Claims, 8 Drawing Sheets

OTHER PUBLICATIONS

Abstract No. 91–334371/46, "Fluid delivery control appts. —exchanges vehicle identification . . . ".

Abstract No. 92–098533/13, "Fluid delivery control appts.—has passive identification module . . . ".

Abstract No. 1997–453545, "Oil refiling appts for motor vehicle—has judgment . . . ".

Bott et al, "The Use of Multisensor Systems in Monitoring . . . "Sensors and Actuators, vol 9, pp. 19–25 (1986).

Jones, E., "The Pellistor Catalytic Gas Detector."

Scott, Jr., et al, "Investigation of the Misfueling of Reciprocating Piston Aircraft Engines," NASA Technical Paper 2803, Mar. 1988.

Demarne et al, "An integrated low–I silicon," Sensors and Actuators, vol. 14, pp. 301–313 (1988).

Oyabu et al, "Intelligent Alarm Detector of Gas Leaks . . . " Paper presented at the $2^{nd}$ Int'l Meeting on Chemical Sensors, Bordeaux, France, Jul. 7–10, 1986.

Lauf et al, "Analysis of liquid fuels using a gas sensor array . . . ," Fuel, vol. 70, pp. 935–940 (1991).

Hoffbeins et al, "Performance of simplified chemical sensor arrays in a neural network–based . . . ," Analysis, vol. 20, pp. 201–207 (1992).

Shurmer et al, "Odour discrimination with an electronic nose," Sensors and Actuators B, vol. 8, pp. 1–11 (1992).

Awards, *Chemistry in Britain,* p. 23 (Jun. 1996).

McCarrick et al, "Fuel identification by Neural Network Analysis . . . ," Anal. Chem., vol. 68, pp. 4264–4269 (1996).

Emco, Wheaton (Margate, England), "Helicopter Refueling Nozzle G457.001" Operating Instructions, Section G, pp. 6–8.

Zapfhähne+, Zapfventile "Fuel Dispensing Nozzles +Spare Parts . . . ," Elaflex Instruction Booklet.

OPW Brochure AFN–85 (Rev. Jan. 1988), OPW Fueling Components (Europe BV) "Aircraft Fueling Nozzles."

Simon & Dannenberg, 1991.

Abstract No. 88–3218280, Gas Sensor Abstracts.

"[Wrong–Filling–Proof Function]".

Abstract No. 96–074365/08, "Oil Mixing prevention device for . . . ".

Abstract No. 94–135719/16, "Appts for measuring and monitoring hydrocarbon fuel quality . . . ".

Abstract No. 93–329651/42, "Fuel discrimination appts. for use with vehicle fuel tank . . . ".

Abstract No. 93–037222/05, "Safety monitoring system for fuel transfer from tanker . . . ".

Abstract No. 92–417515/51, "System appts. for fluid discharge monitor—monitors discharge . . . ".

Abstract No. 90–248838/33, "Device to prevent fuels mixing when filling tank—has obturator in . . . ".

Abstract No. 89–009555/02, "Liq. supply system for supplying liq. to reservoir—has detecting element to prevent erroneous liq. supply . . . ".

Abstract No. 89–001173/01, "Optical sensor for monitoring vapour to liquid ratio in fuel supply—provides . . . ".

Abstract No. 95–351385/45, "Electrochemical sensor with electrode cleaning function . . . ".

Abstract No. 95–337042/43, "Device for testing sample for gas, vapour or volatile material . . . ".

Abstract No. 95–320654/41, "Fabrication of gas sensor for detection of aromas, odours, and volatile material . . . ".

Abstract No. 95–311610/40, "Detection of volatile materials . . . ".

Abstract No. 95–285334/38, "Gas sensor which mimics response of human nose . . . ".

Abstract No. 95–255703/34, "Gas sensor chip for hydrocarbon fuels—combine . . . ".

Abstract No. 93–076658/09, "Sensor appts. for volatile . . . ".

Abstract No. 96–402540/40, "Neural network for pattern . . . ".

Abstract No. 96–300775/30, "Semiconducting organic polymer used in gas . . . ".

Abstract No. 96–268727/27, "Depositing conducting polymer onto tube for use . . . ".

Abstract No. 96–077577/08, "Multi–sensor gas or vapour detector partic. as . . . ".

Abstract No. 96–068944/07, "Semiconducting organic polymer for use in gas sensor . . . ".

Abstract No. 96–068943/07, "Depositing multilayer of semiconducting . . . ".

Abstract No. 96–040352/04, "Condition including device for food or perishable produce . . . ".

Abstract No. 96–040248/04, "Detection of bacteria e.g. *Staphylococcus aereus, Escherichia coli* . . . ".

Abstract No. 96–020678/02, "Sensor esp for gases or vapours, applicable to sampling systems for . . . ".

Abstract No. 96–020677/02, "Sensor arrangement for gases or vapours in such applications . . . ".

Abstract No. 96–171718/17, "Personnel recognition sensor—comprises . . . ".

Abstract No. 95–154953/20, "Detector for odorous substances . . . ".

Abstract No. 93–309721/39, "Method of sensing nature of smell . . . ".

Supplier Accession No.: 96–04032, "Options and approaches to the multivariate . . . ".

Supplier Accession No.: 96–04032, "Electronic nose is an analytical instrument . . . ".

Supplier Accession No.: 96–04031, "Future of electronic noses".

Supplier Accession No.: 96–04031, "Electronic nose for meat and food control . . . ".

Supplier Accession No.: 96–04031, "Evaluation of the electronic nose in . . . ".

Supplier Accession No.: 96–04031, "Use of an electronic nose to detect the source . . . ".

Supplier Accession No.: 96–04031, "History of electronic noses".

Supplier Accession No.: 95–06056, "Use of the electronic nose to evaluate . . . ".

Supplier Accession No.: 95–00437, "Electronic nose for classification of microbial caused . . . ".

Supplier Accession No.: 94–07166, "Electronic nose to measure the environment . . . ".

INSPEC Abstract No.: B9610–7230J–004, C9610–3385–004, "Recognition of fish storage time by a . . . ".

INSPEC Abstract No.: B9609–7230L–010, C9609–3240N–011, "Detection of vapours and odours from a . . . ".

INSPEC Abstract No.: A9615–6855–120, B9608–0520F–024, "A novel method for the preparation . . . ".

INSPEC Abstract No.: A9615–828T–009, B9608–7230–303, "Olfactory sensor array systems . . . ".

INSPEC Abstract No.: A9613–8280T–008, B9607–7230–049, "Multicomponent analysis of heavy metal . . . ".
Conference Title: "8$^{th}$ Int'l Conference on Solid–State Sensors . . . ", Part vol. 3, pp. 36–37 (1995).
INSPEC Abstract No.: B9607–7230L–015, C9607–7410H–026, Grain odour classification with . . .
INSPEC Abstract No.: B9607–2230–001, "Molecular electronics: Prospects for instrumentation . . . ".
INSPEC Abstract No.: B9612–8280T–008, B9696–7230L–039, "Fuzzy neural computing of . . . ".
INSPEC Abstract No.: B9606–7230L–004, C9606–3240N–002, "Biomimetic sensing systems with . . . ".
INSPEC Abstract No.: B9605–7320T–004, C9605–7410H–064, "Electronic noses and their applications . . . ".
INSPEC Abstract No.: B9605–7230L–023, "Sensor array recognition of varieties . . . ".
INSPEC Abstract No.: B9605–7230L–019, "A practical use of electronic noses: Quality estimation . . . ".
INSPEC Abstract No.: B9605–7230L–108, "Screening of irradiated tomatoes by means . . . ".
INSPEC Abstract No.: B9605–7230L–106, C9605–3240D–013, "A calibration technique for an . . . ".
INSPEC Abstract No.: B9605–723L–014, C9605–3240D–011, "Performance definition and . . . ".
INSPEC Abstract No.: B9604–7230–047, "ASICs for integrated sensors".
INSPEC Abstract No.: B9603–2575–033, "Application of conducting polymer technology . . . ".
INSPEC Abstract No.: B9602–1230D–021, "Supervised learning using the vector memory . . . ".
INSPEC Abstract No.: B9601–3240–002, "The electronic Nose and its application . . . ".
INSPEC Abstract No.: B9511–1285–006, "An analogue current–mode . . .".
INSPEC Abstract No.: B9509–7510–020, C9509–7330–311, "Transmission of olfactory information . . . ".
INSPEC Abstract No.: B9516–8280T–101, B9509–7230L–012, "The development of an electronic . . . ".
INSPEC Abstract No.: B9509–7230L, C9509–7410H–010, "Identification of paper quality using a . . . ".
INSPEC Abstract No.: A9516–8280T–006, B9509–7230L–007, "A new generation of integrated . . . ".
INSPEC Abstract No.: A9514–8780B–002, B9508–7230J–002, "Controlled signal transduction across . . . ".
INSPEC Abstract No.: B9507–7230L–021, C9507–3240F–001, "An artificial olfactory system . . . ".
INSPEC Abstract No.: A9512–8280T, B9507–7230L–008, "Recent developments in field–effect gas . . . ".
INSPEC Abstract No.: C9506–7330–167, "Bacteria detection and classification using . . . ".
INSPEC Abstract No.: A9508–8280T–002, B9505–7230–016, Bulk piezoelectric odour sensor array.
INSPEC Abstract No.: B9502–7220–004, "A signal processing ASIC for an electronic nose".
INSPEC Abstract No.: B9501–7230L–006, C9501–7410H–031, "The 'electronic nose' using . . . ".
INSPEC Abstract No.: B9412–0100–79, "IEE Colloquium on 'Application Specific . . . '".

INSPEC Abstract No.: A9424–6817–008, B9412–2860C–048, "Gas sensitivity of modified . . . .".
INSPEC Abstract No.: A9416–8280–014, B9408–014, B9408–7230L–033, "An intelligent gas sensor . . . ".
INSPEC Abstract No.: A8415–8280–027, B9408–7230L–012, "Towards an integrated electronic . . . ".
INSPEC Abstract No.: A9415–8280–026, B9408–7230–016, "A brief history of electronic noses".
INSPEC Abstract No.: A9406–5290–018, "Genetic algorithm design of neural . . . ".
INSPEC Abstract No.: B9406–7230L–006, C9406–7410H–020, "Neural tree network based electronic . . . ".
INSPEC Abstract No.: B9406–7230L–006, C9406–7410H–020, "Neural tree network based . . . ".
INSPEC Abstract No.: B9406–7230L–005, C9406–7410H–020, "Analysis of Electronic nose data using . . . ".
INSPEC Abstract No.: B9403–7230L–012, C9403–3350P–008, "Performance of an electronic nose . . . ".
INSPEC Abstract No.: C9403–7330–150, "Neural network based electronic nose using . . . ".
INSPEC Abstract No.: C9402–3350P–001, "Food and drink industry edging ahead by a nose".
INSPEC Abstract No.: A9401–8280–009, B9401–7230L–006, "Sensitivity enhancement for gas . . . ".
INSPEC Abstract No.: B9311–7320T–001, C9311–1230D–005, "Multi–component gas mixture . . . ".
INSPEC Abstract No.: B9310–723L–008, "From hydrogen sensors to olfactory images . . . ".
INSPEC Abstract No.: B9301–7230L–004, "Artificial olfactory system based on field effect devices".
INSPEC Abstract No.: B9211–7230L–020, C9211–3240D–003, "Integrated semiconductor technology . . . ".
INSPEC Abstract No.: B9209–7230–062, C9209–7410H–026, "Odour discrimination with an electronic . . . ".
INSPEC Abstract No.: B9207–7230L–024, C9207–3350P–002, "Application of an electronic nose to . . . ".
INSPEC Abstract No.: B9205–7230L–007, C9205–7410H–065, "A standalone neural network based . . . ".
INSPEC Abstract No.: B9205–0100–049, C9205–7410–063, "IEEE Colloquium on 'DSP (Digital . . . '".
INSPEC Abstract No.: A91113922, B91065702, "Artificial 'olfactory' images from a chemical sensor . . .".
INSPEC Abstract No.: A91089248, B91052816, "Integrated arrays of gas sensors . . . ".
INSPEC Abstract No.: B90052263, C90051697, "Application of artificial neural networks . . . ".
INSPEC Abstract No.: B90052008, C90053980, "An electronic nose: a sensitive and . . . ".
INSPEC Abstract No.: B90046876, "Basic limitations for an electronic nose . . . ".
INSPEC Abstract No.: B90040307, C90040529, "The fifth sense–on the scent . . . ".
INSPEC Abstract No.: B89025070, C89023149, "Integrated sensor array processing in an . . . ".
INSPEC Abstract No.: B88029354, "Study of semiconductor sensors for an electronic . . . ".

INSPEC Abstract No.: B88009954, "Development of an electronic nose . . . ".
INSPEC Abstract No.: A82116939, "Analysis of discrimination mechanisms . . . ".
INSPEC Abstract No.: B76018044, "Electronic noses to sniff out rogue gases".
Abstract No. 95–351385/45, "Electrochemical sensor with electrode cleaning function . . . ".
Abstract No. 95–337042/43, "Device for testing sample for gas, vapour or volatile . . . ".
Abstract No. 95–320654/41, "Fabrication of gas sensor for detection of aromas . . . ".
Abstract No. 95–311610/40, "Detection of volatile materials e.g. smells, odours . . . ".
Abstract No. 95–285334/38, "Gas sensor which mimics responses of human nose . . . ".
Abstract No. 95–255703/34, "Gas sensor chip for hydrocarbon fuels—combines energising . . . ".
Neotronics Scientific Home Page (www.neotronics.com), "The Electronic Nose".
Neotronics Scientific Home Page (www.neotronics.com), "Sense," vol. 1, No. 1.
Aroma Scan (www.aromascan.com), AromaScan, Inc. (1996).
Lennartz electronic (www.hway.net), "Moses II" modular sensor system.
Chemtech, "Microsensors based on conducting polymers," May 1996, vol. 26, No. 5, pp. 19–25.
Keller et al, "Electronic Noses and Their Applications".
Lewis, N., Caltech; Electronic Nose project (www.gbnet.n).
Barker et al, "Design and Construction of an Electronic Nose . . . ".
Lewis, N., Caltech, "The goal of this project is to compare the response of the Caltech Electronic Nose . . . ".
Pech, L., Chambre de Commerce et d'Industrie de Toulouse, "Sitef 95".
Johansson, S.G., Nordic Sensor Technologies AB, "Development of sensors and software . . . ".
Keller, P., Applications of Neural Networks, Technology Brief "Electronic/Artificial Noses".
Pope, K. "Technology Improves on the Nose As Scientists Try to Mimic Smell," The Wall Street Journal.
Keller et al., "Transmission of Olfactory Information for Telemedicine".
Senior Analysis with ANNs, "Senior Analysis"—References.
Gardner, J., M.D., Newsletter #47, "Sensors and Sensory Systems for An Electronic Nose".
Abstract No. 92(21):155486, "Neural nets 'capture' fuel identities".
Abstract No. 1992:411139, "Performance of simplified chemical sensor arrays in a neural . . . ".
Abstract No. 92(17):127725, "Development of simplified sensor arrays . . . ,".
Abstract No. 1991:539278, "Analysis of liquid fuels using a gas . . . ".
Abstract No. 90(15):111942, "Using sensor arrays and pattern . . . ".
Abstract No. 90(15):111942, "Using sensor arrays and pattern recognition . . . ".
Abstract No. 1991:421288, "Using sensor arrays and pattern . . . ".
Abstract No. 89:3306863, "Gas sensor arrays for olfactory . . . ".
Abstract No. 88(19):155964, "Gas sensor arrays for olfactory . . . ".
Abstract No. 1988:105626, "Intelligent thick–film gas sensor . . . ".
Abstract No. 1988:23790, "An intelligent thick–film gas sensor: development . . . ".
Abstract No. 86(19):152252, "Intelligent thick–film gas sensor . . . ".
Abstract No. 88:3037674, "Intelligent thick–film gas sensor . . . ".
Abstract No. 88:325436/46, "Measuring components of mixt.—using number . . . ".
Abstract No. 1994:200964, "The characterization of volatile . . . ".
Abstract No. 1994:13869, "Integrated tin oxide sensors of low power consumption . . . ".
Abstract No. 94:4704845, "An intelligent gas sensor . . . ".
Abstract No. 1994:22837, "Sensitivity enhancement for gag sensing . . . ".
Abstract No. 1992:465716, "Odor discrimination with an electronic nose".
Abstract No. 1992:446828, "Application of an electronic nose to the . . . ".
Abstract No. 1992:75305, "Warwick electronic case".
Abstract No. 1991:597361, "Integrated tin oxide odor sensors".
Abstract No. 1991:597359, "Integrated arrays of gas sensors using . . . ".
Abstract No. 1990:544552, "Intelligent vapor discrimination using . . . ".
Abstract No. 1990:525790, "Basic limitations for an electronic nose . . . ".
Abstract No. 90:3682949, "An electronic nose: a sensitive . . . ".
Abstract No. 90:3643923, "The fifth sense–on the scent . . . ".
Abstract No. 1990:69198, "The application of discrimination . . . ".
Abstract No. 1987:611211, "Development of an electronic nose . . . ".
"Mass Sensitive Sensors for the Detection of Special . . . ," www.ifak.fhg.de/se_521.htm (1997).
MUPUS Proposal: Deposition Sensors (MDS ODS), www-.saturn.uni–meunster.de/~seifer1/mp415.html (1997).
"Quartz Crystal Microbalance (QCM) Flight . . . " www.jhuapl.edu/cedac/papers/SPIEqcm/qcm.html.
"Protein adsorption with a newly developed . . . " www.fy-.chalmers.se/ap/chp/abst/hook.html.
"Thin Polymer and Phospholipid Films for Biosensors . . . Characterisations . . . " www.anachem.umi.se/~tte/Characertisation.html.
"Thin polymer and Phospholipid Films for Biosensors . . . Characterisations . . . " www.anachem.umi.se/~tte/References.html.
Abstract No. 97–044961/05, "Multi–component quantitative gas analyzer partic. as hand–held monitor . . .".
Abstract No. 97/044960/05, "Amphiphilic substance in fluid matrix detection method using . . . ".
Abstract No. 3032613, "A portable piezoelectric crystal detector for field monitoring..."
Abstract No. 2733008, "The continuous detective of toluene in ambient air..."
Abstract No. 2002291, "Application of a piezoelectric quartz crystal as partition detector..."

Abstract No. 97–065556/06, "Gas sensor combining mass measurement and conductimetric..."
Abstract No. 96–443320/44, "Sensor for detection of organic cpds. or solvents..."
Abstract No. 97–086698/08, "Sensor or detector which can distinguish between various..."
Abstract No. 96–259721, "Fluid identification system for use at filling..."
Abstract No. 95–330001/43, "Method for distinguishing fuel vapours –by comparing relationship of magnitudes..."
Abstract No. 95–310861/40, "Appts. for detection of volatile..."
Abstract No. 94–169033/21, "Polymeric film used for detecting..."
Abstract No. 94–169034/21, "Optical sensor for detecting gaseous..."
Abstract No. 93–329651/42, "Fuel discrimination appts. for use with vehicle..."
Abstract No. 93–017244/02, "Vehicle fueling appts. e.g. for forecourt dispenser –detects..."
Abstract No. 97–189239/17, "Fuel oil type detector for service station..."
Abstract No. 96–4529185/45, "Crystal oscillator e.g QCM used in various..."
Abstract No. 96–452917/45, "Rock crystal disc for crystal oscillator..."
Abstract No. 96–179288/18, "Piezoelectric specific binding assay for detection..."
Abstract No. 95–346215/45, "Apparatus for measuring variation in electrode..."
Abstract No. 95–274496–36, "Natural gas leakage detection between supplier and appliance..."
Abstract No. 94–272155/34, "Fluid specific gravity measuring appts., e.g. for electrolyte..."
Abstract No. 93–322108/41, "Maintaining rate of electroless plating –by using..."
Abstract No. 93–259979/33, "Monitoring system for detecting change in contaminant in..."
Abstract No. 93–258047/32, "Buffered cut quartz crystal –has zinc buffer..."
Abstract No. 93–142495/17, "Simultaneous measurement of mass loading –using quartz crystal..."
Abstract No. 92–348500/42, "Selective chemical sensor –comprises piezoelectric..."
Abstract No. 92–047309/06, "Cryogenic quartz microbalance –has current..."
Abstract No. 91/353398/48, "Early warning reactive gas detection..."
Abstract No. 91–290322/40, "Measuring and controlling deposition on piezoelectric..."
Abstract No. 91–111709/16, "Piezoelectric quartz crystal micro–balance..."
Abstract No. 89–324313/44, "Amplified quartz crystal microbalance immunoassay..."
Abstract No. 89–324312/44, "Enzymatically amplified quartz crystal microbalance..."
Abstract No. 88–105584/15, "Analysing appts. identifying molecular..."
Abstract No. 85–249284/40, "Measuring corrositivity of liquids using piezoelectric crystal..."
Abstract No. 77–50098Y/28, "Soldering quartz mirror to metal substrate –using indium..."
Abstract No. 75–B8885W/07, "Quartz crystal solute mass detector in liquid..."
Abstract No. 73–43510U/31, "Coated piezoelectric analyzers –for fluid"
Abstract No. 65–018385, "An apparatus for analyzing fluids"
Abstract No. 65–017632, "A detector for an analytical apparatus"
Abstract No. 65–015040, "In a piezoelectric fluid analyzer"
Abstract No. 4401693, "Application of photon–correlation spectroscopy..."
Abstract No. 4384835, "Selective detection of organic compounds..."
Abstract No. 4303797, "Transport properties of water and pentane in Langmuir..."
Abstract No. 4303174, "Jet fuel deposition and oxidation: Materials, oxygen, and temperature..."
Abstract No. 4302770, "Further studies of JP–8$\phi$[USAF jet fuel]additive..."
Abstract No. 4331610, "Mass–sensitive detection of solvent vapors. Mechanistic...,"
Abstract No. 4380779, "Studies of jet fuel additives using the..."
Abstract No. 4206361, "Simultaneous application of photon correlation..."
Abstract No. 4206027, "Investigation of jet fuel thermal stability..."
Abstract No. 4200880, "Studies of jet fuel additives using the quartz..."
Abstract No. 4104970, "Use of the quartz crystal microbalance for the study of adsorption..."
Abstract No. 4104226, "Studies of jet fuel thermal stability and oxidation..."
Abstract No. 4102167, "Studies of jet fuel thermal stability and autooxidation..."
Abstract No. 4005973, "Monitoring jet fuel thermally stability using a quartz..."
Abstract No. 3904120, "Monitoring jet fuel degradation using quartz crystal..."
Abstract No. 3831458, "Multicomponent vapor monitoring using arrays..."
Abstract No. 2009750, "Interaction energy between a gas molecule..."
Abstract No. 1833101, "The continuous real–time monitoring of particulate..."
Abstract No. 1800946, "A study of the gas–solid interface using a quartz..."
Abstract No. 3832762, "A sensor for all seasons"
Abstract No. 3631174, "The application of piezoelectric detectors for..."
Abstract No. 3400839, "Chemical piezoelectric sensor and sensor array,"
Abstract No. 3032613, "A portable piezoelectric crystal detector for field monitoring . . . ".
Abstract No. 2733008, "The continuous detective of toluene in ambient air . . . ".
Abstract No. 2002291, "Application of a piezoelectric quartz crystal as a partition detector . . . ".
Abstract No. 97–065556/06, "Gas sensor combining mass measurerment and conductimetric . . . ".
Abstract No. 96–443320/44, "Sensor for detection of organic cpds. or solvents . . . ".
Abstract No. 97–086698/08, "Sensor or detector which can distinguish between various . . . ".
Abstract No. 96–259721, "Fluid identification system for use at filling . . . ".

Abstract No. 95–330001/43, "Method for distinguishing fuel vapours—by comparing relationship of magnitudes . . . ".
Abstract No. 95–310861/40, "Appts. for detection of volatile . . . ".
Abstract No. 94–169033/21, "Polymeric film used for detecting . . . ".
Abstract No. 96–169034/21, "Optical sensor for detecting gaseous . . . ".
Abstract No. 93–329651, "Fuel discrimination appts. for use with vehicle . . . ".
Abstract No. 93–017244/02, "Vehicle fueling appts. e.g. for forecourt dispenser—detects . . . ".
Abstract No. 97–189249/17, "Fuel oil type detector for service station . . . ".
Abstract No. 97–188102/17, "Oil supply appts for motor vehicle fuel tank replenishment—has sensor . . . ".
Abstract No. 97–114893/11, "Oil refuelling equipment for filling gasoline and light oil in motor . . . ".
Abstract No. 97–090485/09, "Oil type detector for service station—comprising two gas . . . ".
Abstract No. 97–082986/08, "Oil recognition device for determining kind of oil e.g. petroleum . . . ".
Abstract No. 97–016970/02, "Gas pump for supplying petrol to car fuel tank—has fuel . . . ".
Abstract No. 96–421506/42, "Fuel properties discrimination system for petrol . . . ".
Abstract No. 96–358182/36, "Oil refuelling appts with oil discrimination function—in which . . . ".
Abstract No. 96–349928/35, "Oil–supplying appts. for motor vehicle service centre e.g. gas station . . . ".
Abstract No. 96–318181/32, "Oil type indicator for vehicle . . . ".
Abstract No. 96–272497/28, "Suspended type refueling appts—has control device which . . . ".
Abstract No. 96–254870/26, "Oil–supply device with oil vapour sensor for gasoline . . . ".
Abstract No. 96–225066/23, "Refuelling appts. for gas station—has fuel vapour sensor . . . ".
Abstract No. 96–175538/18, "Refueling appts. with oil type distinction function . . . ".
Abstract No. 96–167015/17, "Oil supplying device for motor vehicle—has oil type . . . ".
Abstract No. 96–112103/12, "Refuelling device for gas station—has distinction . . . ".
Abstract No. 96–100368/11, "Oil flow mixing prevention device for gas station—judges type . . . ".
Abstract No. 96–100367/11, "Fuel mixing–prevention device for gas–petrol station—uses microcomputer . . . ".
Abstract No. 96–074365/08, "Oil mixing prevention device for underground tank of petrol . . . ".
Abstract No. 96–055427/06, "Oil feed nozzle for petrol- –gasoline station pump—has oil–type . . . ".
Abstract No. 96–043124/05, "Suspended type refuelling appts for vehicle—has oil type . . . ".
Abstract No. 96–023719/03, "Species determin. for fuel oil—by measuring absorbence of permeated . . . ".
Abstract No. 96–016795/02, "Delivery method for liquids e.g. gasoline, kerosene—by storing memory . . . ".
Abstract No. 95–289732/38, "Refuelling device for gas station—uses judgement program to judge type of oil present . . . ".
Abstract No. 95–272425/36, "Refuelling device for gas station—has exhaust control device to intercept . . . ".
Abstract No. 95–260998/34, "Re–fuelling device with oil type discrimination—has gas sensor supplying . . . ".
Abstract No. 95–228297/31, "Refuelling device for gas station—has controller and oil type . . . ".
Abstract No. 94–0077438/10, "Appts. to detect dissimilar oil in fuel oil tank—includes comparator to . . . ".
Abstract No. 97–254907/23, "Vehicle refueling system for gas station—has fuel . . . ".
Abstract No. 97–189254/17, "Fuel oil type detector—has intake coupled to . . . ".
Abstract No. 97–182492/17, "Gas chromatography for continuous sepn. analysis of lower hydrocarbon . . . ".
Abstract No. 95–051340/07, "Hydrocarbon analyte detection method in liq . . . ".
Abstract No. 94–271983/33, "Sensor element for detection of hydrocarbons—has metal wire or foil . . . ".
Abstract No. 97–271372/24, "Method of measuring intensity index of odour—involves notifying . . . ".
Abstract No. 97–229842/21, "Evaluating odour air conditioners—by supplying . . . ".
Abstract No. 97–220738/20, "Odour adjusting apparatus— includes odour detector, device . . . ".
Abstract No. 97–068012/07, "Gasoline distinction device— comprising gasoline detection . . . ".
Abstract No. 96–404764/41, "Appts. for judging condition of fuel—having electrostatic capacity sensor . . . ".
Abstract No. 126:201367 CA, "The online determination of total olefins in gasoline by process gas . . . ".
Abstract No. 126:188176 CA, "Online remote prediction of gasoline properties by . . . ".
Abstract No. 97–384359/35, "Automatic stopping apparatus for filling of tank with . . . ".
Abstract No. 97–346962, "Liquid mixing prevention appts for tanker lorry—has set . . . ".
Abstract No. 97–346961/32, "Unloading control appts for tanker lorry—has controller to . . . ".
Abstract No. 97–346960/32, "Oil supply apparatus for e.g. vehicle—has agreement decision circuit . . . ".
Abstract No. 97–346959/32, "Oil type determining apparatus for e.g. tank lorry vehicle—has oil . . . ".
Abstract No. 97–306405/28, "Tank lorry oil type discrimination function—has controller which . . . ".
Abstract No. 97–290385/27, "Monitoring processes of filling fluids into systems for storing . . . ".
Abstract No. 4406235, "A simplified hydrocarbon compound type analysis using a . . . ".
Abstract No. 4406035, "Monitor valve beats fuelling errors".
Abstract No. 4404265, "New products/Upgraded fuel analyzer".
Abstract No. 97–453545/42, "Oil refilling appts for motor vehicle—has judgement unit which judges type . . . ".
Abstract No. 97–350324/32, "Distinguishing and measuring n– and iso–paraffin(s) and . . . ".
Abstract No. 97–448820/41, "Real–time fluid sensing devices for e.g. non–polar gases—comprises . . . ".
Abstract No. 97–437600/41, "Sensors for volatile materials and gases, useful for differentiating between . . . ".
Abstract No. 97–421382/39, "Aroma sensor for identification of aromatics—has copper phthalocyanine . . . ".
Abstract No. 97–403777/38, "Detector for determining odour concentration in natural gas pressure . . . ".
Abstract No. 97–395669/37, "Object identification apparatus using olfactory sensor system—has array . . . ".

Abstract No. 97–475271/44, "Oil supply appts in petrol station—performs inspection of oil in . . . ".
Abstract No. 97–401916/37, "System for classifying hydrocarbon fuel mixtures—comprises . . . ".
Abstract No. 97–493571/46, "Aroma measuring appts—has gas introduction unit to introduce . . . ".
Abstract No. 97–488310/45, "Odour detection and identification—by comparing characteristic . . . ".
Abstract No. 97–483736/45, "Ultrasonic gas sensor, e.g. for evaluating odour in food and cosmetics . . . ".
Abstract No. 97–521668/48, "Oil supply apparatus installed in petrol station for vehicle—has control . . . ".
Abstract No. 97–450924, "Optical liquid level sensing for aircraft fuel tank discriminating air . . . ".
Abstract No. 98–005390/01, "Odorant concentration measuring apparatus with crystal oscillator type . . . ".
Abstract No. 98–002683/01, "Portable smell monitor for detecting environmental abnormality . . . ".
Abstract No. 98–085783/08, "Controlling flow of liquid from supply line e.g. oil or gasoline line to . . . ".
Abstract No. 98–178124/16, "Fuel dispensing system for aircraft—has control . . . ".
Abstract No. 98–207014/18, "Sensor for detecting chemical analyte in fluid—comprises . . . ".
Abstract No. 97–350324/32, "Distinguishing and measuring n– and iso–paraffin(s) and . . . ".
Abstract No. 95–223963/29, "System for analysing total scanning fingerprints of complex . . . ".
Abstract No. 3807340, "Derivative spectroscopy as an analytical tool for hydrocarbon identification,".
Abstract No. 98–178482/16, "Tagging hydrocarbons for subsequent identification—by using . . . ".
Abstract No. 1999–105323 [09] WPIDS, "Raman spectroscopy for determination of hydrocarbon . . . ".
Abstract No. 1999–204396 [17] WPIDS, "Integration circuit for use in analyte detection and identification . . . ".
Abstract No. 99–153270/13, "New chemical sensors and arrays—comprising a mixture . . . ".

* cited by examiner

TESTING DEVICE AND METHOD OF USE

This is a continuation of PCT application PCT/GB97/02951, filed Oct. 28, 1997.

BACKGROUND OF THE INVENTION

The present invention provides a testing device and a method of its use, in particular for distinguishing between hydrocarbons.

There are many occasions when liquids are to be mixed commercially on a large scale and/or frequently, in particular distillate liquid products in a refinery or derived from a refinery, and it is essential that the correct liquids are mixed. Examples of such mixing occurs during transfer of fresh product e.g. gasolines or kerosenes to replenish tanks containing previously made product, as well as the dispensing of propulsion fuel e.g. motor gasoline or aviation gasoline, marine fuels, jet fuel or diesel into tanks of appropriate vehicles e.g. cars, lorries or piston or jet aircraft. The consequences of mis-fuelling are at best a nuisance and at worst lethal in the case of aircraft. In particular it is essential to be able to distinguish easily between aviation gasoline and jet fuel, or between motor gasoline and diesel. Existing methods involve use of a number of different techniques e.g. different colours and labels, audible warnings, and different nozzle sizes.

A device and method have now been found to achieve the distinction quickly, easily and routinely.

DESCRIPTION OF THE INVENTION

The present invention provides a method for controlling the movement of a liquid preferably comprising a liquid hydrocarbon from a first location to a second location, via closure means capable reversibly of moving at least partly (and preferably completely) between an open and a closed position, at least one of said first and second locations having a vapour space, and preferably at least one of the first and second locations having a vapour space above the liquid, which process comprises analyzing the vapour in one or both locations, comparing the results of the analysis(es) with a standard or each other, and using the results of the comparison to control the movement of the closure means. Preferably the first location has vapour space above the liquid and the second location has vapour space, optionally above a liquid, and the process especially comprises analyzing the vapour in or from the second location and optionally in or from the first location comparing the results of the analysis in or from the second location, with a standard or the results from the analysis in or from the first location.

The invention also provides an apparatus for controllable passage of a liquid which comprises a first zone containing said liquid, a reversible closure means, a first line between said first zone and said closure means, a second zone defining a vapour space for vapour of said liquid and optionally also said liquid, a second line from said closure means to or into said second zone, at least one detector for analyzing vapour in or from said second zone and/or above liquid in said first or second zones, means for transmitting the data from said detector(s) to processing means for comparing said data from one of said zones with a pre-set level or with data from the other of said zones, means for controlling movement of enclosure means, operation of said processing means and said controlling means being dependant on said comparison.

The present invention also provides a modification of said apparatus in which said second line passes into said second zone but is not integral with it and said detector is inside or preferably outside said second line and analyzes the vapour from said second zone. In this case the second line preferably has mounted on or in it said detector, and may be reversibly inserted into said second zone and the vapour analyzed. The second line provides the line for transporting the liquid as well as a support for the detector.

The present invention also provides an apparatus for dispensing a liquid e.g. a hydrocarbon such as a fuel which comprises a nozzle for inserting into a tank containing vapour e.g. a fuel tank, a reversible closure means preferably valve in said nozzle or in a feed line thereto for control of dispensing of liquid e.g. fuel, a detector for contacting the vapour from or in the tank, e.g. for insertion into said vapour, said detector being preferably capable of being in vapour contact with the dispensing end of said nozzle, means for passing a signal from said detector to a processing means for comparison of said signal, and a controller receiving output from said comparison for controlling movement of the liquid e.g. fuel, e.g. allowing or stopping its movement, preferably using said valve.

The invention will be described with respect to differentiating between fuels, but is applicable to other liquids as described below.

The movement of the liquid from the first zone to the second may be from a tank, a bulk one such as a non movable one e.g. an underground fuel tank via a fuel dispenser e.g. nozzle or bowser into a tank of a movable vehicle e.g. one powered by a combustion engine, as at a gasoline or rail car filling station, or an aircraft or boat, ship or tanker refuelling point or cargo loading point. The first zone may also be in a tank or pipe and the second zone a tank, e.g. for passing fresh gasoline feed components or blended gasoline to fill a partly full tank of previously made material, for example in a tank farm or from a fuel tanker into the pipes and tank of a filling station or from a tank on land and pipes into a ship tank. The first zone may also be in a tank and the second in a pipe, leading elsewhere in a refinery e.g. moving gasoline from a tank to a second location for subsequent blending. The first and second zones may also be in refinery pipes. In the case of pipes, there may be head space above the liquid level in which vapour is present and can be analyzed. The tanks are usually storage vessels for the liquid, either stationary as in underground or above ground repositories for fuel, especially ones periodically filled with fuel, e.g. from sea, rail or road tankers or fed directly by pipeline e.g. in/or from a refinery, or moveable in transport vehicles for propelling them e.g. in cars, lorries or boats or for containing them e.g. in gasoline road rail or sea tankers. Thus the tanks may be storage vessels or containers for long or short term retention of fuel.

The liquid being moved into the second location is one whose vapour is different from that of a liquid which it is not desired to be present in the second location e.g. because they are incompatible with each other or more usually because of the unsuitability of the undesired liquid in that second location. An Example of the latter is when the second location is a fuel tank for powering a combustion engine, for which one or more liquid fuels cannot or should not be used.

The liquid being moved preferably comprises a hydrocarbon which is liquid at 25° C. e.g. fuel, lubricant or crude oil containing partly volatile hydrocarbons, e.g. of 4–20 such as 4–10 carbons and usually aliphatic or aromatic, and possibly also non-hydrocarbon components, such as oxygen compounds e.g. ether octane boosters or phenols, or antioxidants, nitrogen compounds such as inhibitors/ dispersants or cetane improvers such as organo nitrates and/or sulphur compounds e.g. impurities in the fuel, and/or perfumes and/or octane boosters e.g. organo leads.

The apparatus and method can also be used to distinguish between hydrocarbon liquids e.g. different types of crude oils, different kinds of gasolines e.g. leaded/unleaded or super unleaded fuels (with non lead octane boosters) or oxygenated/non oxygenated fuels, e.g. ones containing oxygen such as ethers e.g. MTBE, ETBE or TAME or alcohols, or feedstocks therefor e.g. reformate, alkylate etc. middle distillate fuels e.g. kerosene, diesel and fuel oils or bunker fuels such as marine fuel, heating and electricity generating oils. Other examples are the distinction between high sulphur diesel oil (e.g. a residual fuel) and low sulphur diesel oil e.g. a middle distillate, the diesel oils containing more or less than 0.05% of sulphur containing compounds (expressed by weight as sulphur). Diesels of nominally the same grade e.g. cetane number but containing different compounds may be differentiated. Further examples involve distinction between gasoline, e.g. motor gasoline, paraffin (or gas oil) diesel and heating oil, e.g. in an agricultural environment; the order from gasoline to heating oil is the order of decreasing volatility. Distinction between hydrocarbon fuels e.g. diesel and biofuels e.g. esters of long chain acids e.g. rape seed oil can also be made. Other examples in the petroleum industry are diffentiating between lube oils e.g. synthetic and by hydrocarbon oils, and between heat transfer oils. Further examples of liquids are different types of solvents or reactants used in chemical, petrochemical or pharmaceutical industries.

The liquid to be moved may be liquid at 25° C., either under atmospheric pressure, or under higher pressures e.g. a liquefied gas, such as liquid petroleum gas (LPG, predominantly butanes) and compressed natural gas (CNG, predominantly methane). Preferably liquefied gases are moved at reduced temperature e.g. −200° C. to 0° C. such as when the invention is used to distinguish between liquid nitrogen, liquid oxygen and/or liquid air, or between LPG and SNG. The liquid to be moved may be under a pressure less than atmospheric in order to increase its volatility and hence the sensitivity of the sensors. The liquid being moved may be at raised temperature e.g. 50–200° C., in order to decrease the viscosity or because its melting point is above 25° C., examples of this use are between bitumens or between petroleum waxes or other materials solid at 25° C. but distinguishable from their vapours.

The invention may be aimed at ensuring that the vapour over the first zone is the same as in the second zone i.e. that the liquid passed into the second zone is the same as that previously present in the second zone. It is therefore important that the liquid does not flow, e.g. closure means remains closed, if the vapours are different or if the vapour in the second zone does not otherwise meet a particular standard or threshold. It is particularly important to stop the mixing of a liquid from the first zone with vapours of a different liquid in the second zone when the initial boiling points of the liquids under atmospheric pressure differ by more than 100° C. especially more than 135° C., in particular when one of the 2 liquids is aviation gasoline, e.g. comprising isopentane or butane with iso octanes, and/or aromatics such as toluene, and the other is jet fuel comprising kerosene, or alternatively when one of the liquids is motor gasoline or a component thereof and the other is a diesel/gas oil/vacuum gas oil/fuel or bunker oil fraction. The invention is of particular value to enable distinction to be made between gasolines, and hydrocarbons with initial atmospheric boiling points of at least 140° C. especially at least 170° C., or hydrocarbons having a boiling point of at least 250° C.

The movement is stopped by the closure means, which may be a valve, in which case any movement is otherwise impelled or propelled by gravity or a pump, or the closure means may itself comprise the pump, acting as valve and pump.

Alternatively the movement may be allowed by operation of closure means for liquid moving in a different line from a line between the first location and second location as with a flow diverter or closure of a valve in a recirculating liquid stream forcing the liquid to flow via a different route i.e. between the 2 locations. The movement may be stopped by the presence of an unopen closure means which has fail safe arrangement such that it cannot be opened at all unless another criterion is met e.g. an engine running to pull vacuum on the closure means allowing it to open if required as in a vacuum lock. The closure means e.g. valve may be in or near to the liquid dispenser e.g. the nozzle as is preferred, or upstream thereof and in contact therewith (e.g. in a separate housing from the dispenser); the closure means may also be in or near the dispensing pump. The separate housing may also comprise processing means second signal passage means, controlling means and a second valve controlling movement of said liquid. Preferably the controlling means is activated before any liquid is passed, rather than allowing a small amount of liquid to pass before the controller checks it is the "correct" liquid. The control decision may be passed to the closure means to open or shut a valve or operate a relay or a pump, by pneumatic means or electromagnetic radiation e.g. radio, light, laser means, such as use of light down optical fibres. Preferably the closure means stops liquid flowing, unless it receives the "correct" instruction to open, rather than the reverse. If desired a decision that the liquid to be passed from the first to the second zone is the "wrong" liquid and therefore is stopped from flowing may activate an alarm e.g. an audible and/or optical waning.

The detector for analysing may be in a vapour space above a tank, or in an entry neck thereto or, in the case of a line, in its top or better in a small extension over the line with head space. If desired a sampling point may be present over a liquid line, into which sample zone a portion of liquid may be drawn (and hence vapour produced). The latter may be useful for safety purposes especially to seal off the sample and detector zone from the line.

In the analysis, the nature or total concentration of one or more vapour components may be obtained or both the concentration and nature of the vapour components may be found. The output signal from the analyzer is passed to the processor e.g. a mini computer usually by wire or radiation to process the data and instruct the valve what action if any to take. In relation to the former approach the total concentration may be obtained as a single signal e.g. from the second zone, and this may be compared either to a fixed reference point or a standard concentration or to the corresponding value for the vapour in the first zone. In the comparisons, compensation means may be included e.g. in the controller to correct for differences between the temperature of measurement e.g. in the second zone and the fixed reference point or standard or first zone. Thus at a temperature of measurement of 35° C., avgas vapour concentration for example would be high but so would the kerosene vapour concentration so compensation for this is usually desirable. A comparison may be made so that action is taken to open the valve/operate the pump when the signal is above a level of background noise, or above any chosen level e.g. 10% above base, or part way e.g. 25–75% between the level for the fuel in the first zone e.g. gasoline and that for a fuel which should not be present in the second zone e.g. diesel; thus a signal above say 50% between the levels would allow the gasoline to move while one less than 25% would stop the movement as it would show the presence of diesel in the second zone. Alternatively if diesel were in the first zone, signal from the second zone above the desired level e.g. due to gasoline would stop movement of the diesel. In a similar way if the amplitude of the signal from the first zone were within given tolerances the same as that from the second zone, the liquid could pass, but not otherwise.

The key when considering analysis for the total concentration of one or more vapour components is that the signal from the second zone should be above or below a threshold value in order to allow liquid to move, being above the threshold when the amplitude of the signal from the second zone for the desired liquid is above that of the non desired liquid, and below the threshold in the reverse case.

The invention is particularly applicable when frequent connections are made in dispensing of liquids, in particular when the dispensing can be from one of a number of tanks of different liquids, into a number of different second locations; an example of this is the feeding from a multi-compartment tanker e.g. (road, rail or boat tanker) into a number of separate tanks e.g. at a filling station or the feeding from one or a number of different tanks into a number of different tanks e.g. of vehicles.

The analysis may be by nature of one or more of the components in the liquid to help distinguish more finely between liquids. In this case the detector (or detectors) provide more than 1 signal, which can provide a finger print or pattern characteristic of the liquid and special computer techniques e.g. chemometric analysis such as regression techniques e.g. Principal Component Analysis or Cluster Analysis or Neural network analysis can be used to compare the liquids. Again similar analysis within tolerances to standards or above fixed levels or comparison with other liquids would allow passage of the liquid. Preferably, however, only the total concentration of vapour is measured for ease of operation and simplicity. Thus when the analysis is of total vapour concentration or is specific to at least one compound present in said liquid, the comparison of the results of the analysis controls movement of the closure means depending on whether the total vapour concentration or the amount of said compound(s) present respectively is above or below a defined level.

The output from the processor is usually a go signal to instruct the controller to open the valve or allow it to open or activate the pump, or no signal or a no go signal to close the valve or not allow it to open. Once the signal has been passed any subsequent change in the concentration of vapour usually does not trigger a fresh signal. So a high concentration of vapour can trip a go signal but a subsequent reduction usually does not trip a no go signal; by this means once the vapour in the second zone has been "recognized" as correct, the flow of the liquid can be governed by any manually or remote operated valve without risk of the detector signal overriding it. The controller usually acts almost instantly e.g. whenever the sensor shows the "correct" liquid, but may have an in-built delay, which may be useful e.g. when scheduling blending operations for a refinery tank farm moving components to or from a tank. In this latter case the controller usually has a memory, a memorized reading from the sensor for comparison with a preset level and a go/no-go logic. The closure means activatable by the controller may be upstream of the pump i.e. between tank and pump, as may be the case with a number of tanks separately feeding a single pump, but is preferably at or in proximity of the fuel dispenser. In the latter case the closure means may be separate from the dispenser and upstream, e.g. in the form of a separate fitting retro fittable between the dispenser and its feed line from the pump. The valve may otherwise be part of the dispenser (see below), or downstream of the dispenser e.g. in a sheath retrofittable with the entrance to the receiving tank, of a vehicle such as an aeroplane, car or boat (see below).

The benefit of the method is that it stops mis-fueling or mixing between liquids, usually of widely different boiling point and hence concentration of vapours therefrom. The control can be on line or at line.

In an embodiment of the method of the invention, the first location may have a vapour space optionally above the liquid, and there is a vapour space at the second location, which may or may not also be above a liquid and may or may not contain vapour. The vapour at the first location can be analyzed and compared to a standard, the standard being for the liquid desired to be moved to the second location; an example of this is the filling of empty clean tanks with a specified fuel from a store. The standard may have been preset or relate to the last vapour at the second location (e.g. with a time delay). The vapour at the second location can also be analyzed and compared to the standard, there being no vapour above liquid at the first location.

The overall apparatus can be integral with no relative movement of the parts apart from any movement of the closure means or movement due to use of flexible lines; an example of this is the transfer of fuel in integral lines from a first line or tank to another line or tank. The apparatus may also be non integral e.g. with relative movement of the second line and second zone. These may be releasably joined e.g. with clips, as in the case of dispensers for diesel or fuel oil temporarily joined to input lines for tanks on land, or in vehicles or on ships or for aviation fuels temporarily joined to input lines in aircraft. The second line and second zone may also not be joined, but moved in and out thereof. This is the case with a fuel nozzle removed from a holder e.g. in a fuel "pump" stand in a filling station and inserted into a fuel tank of a vehicle. The nozzle can carry the detector into the second zone.

The detector can also be mounted in or especially on an extra tube which can be temporarily joined to the nozzle e.g. as a sheath surrounding the nozzle end, which may be locked in place, or by a clip on the extra tube onto a corresponding flange on the nozzle or the reverse. The extra tube has in it a valve movable between open and shut position on instruction from a controller. The extra tube may also not be joined to the nozzle but may be separate from the tank but capable of being carried with the tank, or may be releasably or non releasably attached to the tank e.g. in its neck. The extra tube may be adapted to surround or be surrounded by any sieve present in the nozzle or entry to the tank, e.g. outside a frustoconical sieve, the valve being a flap in the bottom of the extra tube. In this way the detector may be associated with the tank providing the second location and hence be carried by the vehicle/aircraft/boat etc i.e. with the second zone, in which case the processor and controller may be similarly carried. A negative signal from the processor would ensure the valve remained shut. By this means, the vehicle/boat/plane etc carries with it all the equipment needed to stop entry of the "wrong" liquid, without having to rely on equipment in association with the fuel source i.e. the tank on land or in the filling or refuelling station. Such arrangements with the extra tube are easy to retrofit to existing systems.

If desired the extra tube may have a number of detectors each capable alternately of being brought into contact with the vapour, with means, e.g. externally mounted on the tube, of bringing each detector in line. Thus a rotatable disc externally carrying identification of each of the various vapours to which each detector is sensitive may be used to allow the vapour of the desired fuel feed to contact the appropriate detector. Thus dialing the appropriate fuel on the disc on the extra tube would give the user freedom to allow that fuel to fill the tank. This approach would be valuable where the nature of the fuel in the dispensing tank is unknown or not known with certainly, or one dispensing device is fed by more than one dispensing tank.

The apparatus may comprise a line passing from a first to a second location which are separated by a reversible closure means e.g. valve. A pump separate from the valve may be present in said line or upstream of the first location. The detector may be in the vapour space over the first or preferably the second zone or especially temporarily in the second zone i.e. near the end of the line inserted into said zone. The detector provides a signal(s) to the processor which passes a signal to a controller which activates the valve/pump. The signals may be sent by wire or fibre optics or by electromagnetic radiation, especially infra red, microwave or other radio waves. Advantageously where the fuel dispenser comprises a nozzle and fuel control valve, as well as a detector, the detector can pass the signal to a processor also comprised by the dispenser by wire or fibre optics or radiation, and hence to a controller for activating the valve. When the controller and pump or valve, or processor and controller are separated by a fuel conducting line, passage of a signal between them may be by wire line but is preferably by fibre optic line or electromagnetic radiation.

When the detector is only to be temporarily inserted into the second zone, the detector may be inside the second line, but preferably is outside the line but mounted on it, so it can detect the vapour of the second zone separately from any residual vapour from the second line. In this case the apparatus can comprise the second line comprising the nozzle with analyzer, together with a control valve activated from the analyzer results, a pump for pumping the liquid and a second valve e.g. manually operated for dispensing the fuel; the line from pump to the nozzle can be rigid or flexible or articulated.

The present invention also provides a fuel dispenser which comprises a nozzle for exit of the liquid e.g. fuel, a conduit through the dispenser for the liquid e.g. fuel, a valve in said conduit urged to a closed position by urging means but releasably openable against said urging means, a manually operatable actuator to open said valve, a vapour detector comprised by said dispenser adapted to be in vapour contact with vapours at the exit end of said nozzle, means for passing the output from said detector to a data processor and means for controlling said valve from the output of said processor. In this form the dispenser itself has the control means capable of stopping flow of "incorrect" fuel rather than the control means being separate from the dispenser e.g. with the pump in the fuel stand in the filling station which would need also means for passing the signal output from the controller to the valve/pump back to stop the flow, e.g. along a wire associated with the line for fuel from pump to dispenser.

When the detector is not itself in or moved into the second zone, it is preferred to withdraw the vapour from the second zone to the detector. Thus especially in connection with movement of liquid from a non movable tank to a tank of a movable vehicle, the vapour in the second location is analyzed by withdrawing it past a detector associated with a dispenser for the liquid comprising a releasable valve, said dispenser being in a liquid line between the first and second location. The dispenser preferably has a nozzle, an internal liquid conduit a valve and a body portion and the detector is located in or on the nozzle, between the nozzle and body portion or in the body portion.

The dispenser usually has the detector in a protective housing, which in the case when the detector is inside the nozzle, may be open towards the outer dispensing end of the nozzle, and in the case of the detector inside the nozzle, the housing is preferably not open towards the inside of the nozzle. By this means the detector has reduced contact with liquid fuel rather than fuel vapour. Preferably the dispenser incorporates means for purging the detector of vapour after use e.g. by use of air or an inert gas after the dispensing of fuel has ceased and/or a liquid level detector to shut off flow of fuel when the level in the tank is sufficiently high or frothing occurs at the tank entrance. Such a liquid level detector may comprise a hollow narrow tube inside the nozzle separate from the fuel and extending from the dispensing end of the nozzle to its head end, where a conduit leads from that tube to a safety anti-tilt device causing fuel flow cut out, if the nozzle is on its side e.g. on the floor. This device may be a ball which moves in a restricted space between a location allowing free movement of vapour in the conduit to a location where the movement is stopped because the ball blocks an exit hole for vapour. The liquid detector has an automatic cut out releasing the valve to its closed position in the event of decreased air pressure in the hollow tube and conduit from the rise in liquid level due to overfilling or frothing. The vapour detector may be located inside the above narrow tube, or preferably in the housing of the safety device or automatic cut out. The signal leads from the vapour detector may pass to a processor and controller also in the dispenser e.g. in the housing, or may return to the pump fuel stand; preferably the signals are sent by electromagnetic radiation but may be sent via wires or optical fibres, which may extend longitudinally in or on the walls of the fuel line between dispenser and pump. The automatic cut out means usually comprises the narrow tube to the nozzle, the conduit, which often contains the anti tilt device, an enclosed chamber with an internally spring loaded diaphragm constituting one wall, the chamber operating into a further thin passage extending longitudinally in the dispenser, separate from the fuel, the passage leading to a fine tube ending in the throat of the valve seat, against which the dispenser valve is urged in its closed position. The cut out means operates by passage of the fuel through the throat on depression of the dispensing handle causing by a Venturi effect a reduced pressure in the fine tube which causes suction all the way through to the narrow tube in the nozzle; if the latter tube is open, the pressure drop in the line is small and air is freely drawn through from the narrow tube to the fine tube and into the throat. If the narrow tube is blocked e.g. by liquid in the case of frothing, the pressure is rapidly reduced causing the diaphragm to more inwards into the chamber. The movement causes movement of an external blocking pin or rods to which the diaphragm is externally attached, the pin or rods restraining movement of the dispenser valve back to its valve seat. Thus the sensor can be used to block the mechanism of the automatic cut out, resulting in cut out and valve closure. Thus the operation of the automatic cut out draws the vapour from nozzle end to the detector in the line of the cut out mechanism.

The sensor or processor may send the signal to the processor or controller respectively and hence the pump to activate or stop the pump, or engage/disengage a locking device on the manually operatable activator e.g. dispenser trigger or may send a signal to activate the valve in the dispenser itself. In the last case, the dispenser may, as described above, have already an automatic cut out, which is usually in the form of a pressure activated diaphragm or similar device, which on activation results in release of a spring resulting in closure of the valve. The sensor may send the signal to a processor controlling the activation of the diaphragm; thus the sensor signal may activate an induction coil causing a ball or rod e.g. in an anti tilt device to move and hence move the diaphragm. Alternatively the processor may activate a pump to open a sensor valve in the hollow liquid level detector tube. In this case the sensor may check the vapours from the tank and, if acceptable for the fuel to be fed through the valve and dispenser (e.g. both are jet fuel), then the sensor valve may open, allowing the manual operation of the dispenser in the usual way; if the sensor finds the wrong fuel in the tank compared to the input feed lines, then this sensor valve remains closed, thereby causing the automatic cut out to operate i.e. via the diaphragm to keep the dispenser operation blocked. In a third operation the processor noting a signal for the wrong fuel may cause creation of a pressure difference e.g. in the hollow liquid level detector tube, thereby activating the cut out, and hence not allowing fuel flow; the pressure difference may be created by activation of a pump or other movement of air or operation of a flap or mini valve in the detector tube.

With some dispensers, the automatic cut out may not be needed for safety reasons, but a cut out mechanism comprising the hollow tube, housing for the cut out and diaphragm and associated springs etc. may be used instead for the analysis, location of sensor, and control of the invention. Hence, the hollow tube may lead to the housing, where the sensor is located, as well as or instead of the diaphragm. The activation by the sensor may result in movement of the diaphragm, overriding the manual operation of the flow valve. The diaphragm (and hence the valve) may be released by the safety device, automatic cut out and/or vapour detector.

In this latter embodiment of the dispenser the detector may be in a head portion of the dispenser e.g. in association with the diaphragm, such as to override and trip it. Advantageously however the detector is in a position in relation to the narrow liquid level detector tube upstream of the head portion of the dispenser, which comprises the valve and diaphragm. In this case the nozzle and head portion of the dispenser may be separated by a hollow boss or collar or annular chamber having a core for passage of the fuel and optionally a separate hollow tube or channel adapted to be located in relation to corresponding tubes or channels in the nozzle and in the head end. The boss, collar or chamber also comprises a detector e.g. one located in an enclosed chamber therein open to the tube or channel, as well as a processor taking a signal from and analyzing the results from the detector and for activating means to stop passage of the vapour in the tube of channel to the automatic cut out, e.g. a controller to act on instructions from the processor. In this way the detector and processor and stopping means may be in an annulus in the boss, chamber or collar, which is separate from but in use engageable with the nozzle and head portion. Such an approach makes easy retrofitting of the detector, processor and stopping means to an existing nozzle and head portion with automatic cut out. Usually if the dispenser has an automatic cut out the sensor will activate the cut out when the incorrect fuel is detected, but when the dispenser is not so fitted, then it usually will pass a signal by radiation electrical wire or fibre optics to the pump housing to stop passage of fuel.

The collar or chamber in the dispenser may be annular or toroidal in shape, and may optionally be reflective inside e.g. coated with reflective metal e.g. silver. The vapour passes into the chamber. Through it may be directed analyzing radiation from a source, going round the annulus and to a detector located upstream of the entry of the radiation, to give the radiation a long and relatively constant path length. The collar or annular chamber may have a perforated wall e.g. the outward facing end or diameter thereof; the vapour may then enter through a circumferential surface or an inward facing diameter pass through the device past the sensor and pass outside through the perforated face. A mechanical piston, activated directly or indirectly by movement of the nozzle into the tank, may effect aspiration of the vapour through the chamber, particularly when no automatic cut device is provided.

The dispenser may also comprise a sheath or bellows at least partly longitudinally surrounding the dispenser e.g. surrounding the nozzle down to its dispensing end; there may also be a means for sucking vapour past the handle end of the nozzle which means may be comprised by the dispenser or be distant therefrom e.g. back at the pump and connected to the dispenser by a line part of or attached to the fuel hose line. Such sheaths or bellows are used in vapour recovery systems. In this case the detector may be present between the sheath/bellows and the nozzle, e.g. mounted towards the handle end of the nozzle, rather than the dispensing end. The vapours from the second zone are thus withdrawn past the nozzle and analyzed there, rather than analyzed in the zone. Thus the sheath or bellows e.g. of flexible plastics material may be collapsible in the manner of a concertina about the nozzle but be close fitted to the dispenser body near the manual actuator on the lower side of the dispenser, and with a rigid walled channel on the upper side of the dispenser, the channel leading e.g. to suction means for vapour recovery. In the channel the sensor may be located to be acted upon by the vapour. The sheath or bellows may have a toroidal end with rigid material to reinforce it and/or weigh it down e.g. a ring or sections thereof of rigid plastic or plastic covered metal, and the sheath may be separated from the nozzle by one or more separators loosely surrounding the nozzle. In this way insertion of the nozzle into the tank collapses the sheath or bellows but allows an adequate seal to the body surrounding the tank e.g. the side of the vehicle. Alternatively the sheath or bellows may lead to a sensor within the annulus surrounding the nozzle, but not mounted on the upper side of the body of the dispenser. In this embodiment the sheath or bellows is a pendant skirt surrounding the nozzle and ending in the weighted or reinforced end. Above the collapsible skirt is a rigid sheath fixedly surrounding the nozzle and having therein the sensor e.g. in a toroidal or annular form, with inward or downward facing perforations to allow entry/exit of vapour, and optionally outward facing perforations to allow exit of vapour. The weighted part of the collapsible skirt may be attached to one or more rigid elements extending axially and internally, or especially externally, of the sheath to the rigid sheath, wherein it may operate mechanically an activator for the sensor e.g. generator or flap or window opener, or may be used to aid removal of vapour; in this latter approach the element may close over the outward facing perforations when the skirt is non collapsed (to help protect the sensor from the environment) but may be moved axially relative to the perforations so a slot or hole in the element may register with the perforations, thereby allowing exit of vapours.

Many forms of detector or analyzer device can be used to determine the total concentration of vapours and optionally their nature(s); the detectors or analyzers can usually detect amounts of more than 0.1 ppm preferably more than 1 ppm of the vapours. Among suitable detectors are spectroscopic and gas chromatographic devices, and olfactory sensors (also called "electronic noses"). The device may be at the site of the pipe or tank etc, though for safety purposes the device may be separate from its detector or sampling head and joined thereto by an analysis line, either for the sample (i.e. for taking a sample of the vapours from the site) or for the signal (e.g. down an optical fibre line). The device can be activated, ready for use, by a prior action of the user, in particular the removal of the nozzle from its location in a fuel pump stand in a filling station, so that the removal will release a depressed arm starting the pump, as well as activate the device e.g. apply power thereto or warm it (if required), or open an optical shutter in a spectroscopic detector. The detector or analyzer device may be battery powered, the battery(ies) being recharged by induction on return of the nozzle and thus detector to the "pump" receiving location when waiting for use, or the device or battery may be attached to one or more solar cells e.g. mounted on the dispenser upper surface.

The detector or analyzer device when comprised by the dispenser may be primed ready for use by prior action of the user on the dispenser. This action may be by depression of a button on an exterior surface of the dispenser such as on its top or head portion or by depression of a spring loaded annular arm surrounding the nozzle and hinged to the distant side of the nozzle or by depression of a spring loaded arm provided with 2 leg portions extending on either side of the nozzle which are hinged to opposing sides of the nozzle, the depression resulting from contact with the tank fuel opening or by movement of the handle of the dispenser, against the urging means, depression or movement causing closure of a battery circuit for the device or generating a priming current for the device. In the case of the handle, the initial movement against the urging means may prime the device, which analyzes the vapour, passes a signal to the processor and hence to the controller and valve. With fast acting detectors the delay between depression of the handle and flow of fuel (assuming a "correct" fuel) would be negligible. Use of such a priming system could increase the lifetime of any battery or reduce its size or even avoid need for its use.

The dispenser may also comprise means for activating the sensor, which may be an elongate member e.g. arm which is moveable between a rest position when the dispenser is separate from a tank, and a closed position when the nozzle is inserted into a fuel tank and the dispenser urged into contact with the surround to the neck of the tank; the act of urging moves the activating means to the closed position. The activation means may operate a generator to power the sensor and/or processor/controller or charge a battery therefor, or may mechanically operate means to bring vapour and the sensor in contact, preferably by moving vapour to a stationary sensor, e.g. operating a piston to suck vapour past a sensor, or opening a cover over a sensor (either directly or indirectly) allowing vapour to contact the sensor, or moving a sensor into contact with the vapour. Thus an activation lever e.g. a depressable arm can be connected mechanically via levers pivotally to move a piston in a tube, the tube upstream of the piston being air and downstream of the piston being the vapour to be tested, and the piston is moved past a recess or side arm to the tube, in which recess or arm a sensor is located. As the arm is depressed, the levers move the piston which sucks vapour behind it and when the piston moves past the recess or side arm, the vapour is drawn in contact with the sensor. When the nozzle is removed from the tank the depressable arm returns to its rest position moving the piston and hence withdrawing the vapour from the sensor and the tube, thereby purging it to reduce contamination when the nozzle is used again.

The piston may also on its return move vapour out of the tube, e.g. when the tube has a one way entry valve to stop egress of vapour but allow entry and also separately a one way exit valve to allow exit of vapour but deny entry; by this means too the sensor zone may be purged of vapour.

The activation lever may also mechanically move a flap or uncover a window thereby revealing the sensor to the vapour; the window may be in a slatted component adapted to move with respect to its frame between a closed piston covering the sensor and an open position uncovering the sensor. The frame itself may comprise slats, but with one or more of the holes in the slats revealing the sensor.

If desired the activator lever can be part of or an extension of the manually operated activator for the main dispenser valve. In this case squeezing the activator also moves the piston drawing vapour into contact with the sensor; the main dispenser valve in this arrangement is adapted not be moved until after the piston has been moved, the vapour registered by the sensor, and its nature accepted.

Among the possible spectroscopic techniques are infra red (both mid and near IR), ultraviolet and fluorescence spectroscopy and nuclear magnetic resonance (NMR) included pulsed NMR. In each case the vapour passes into or through an open or closed sample cell, and a beam of the appropriate radiation is passed through it and all or part of the spectrum is taken optionally with the aid of refracting or reflecting means e.g. a mirror(s) or prism(s) to multiply increase the path length and arrange the source next to the detector. The IR technique can use a single diode detector or a single multi diode detector, optionally with a filter selective to allow only certain wavelengths through it from the sample onto the detector; the selective filter is particularly important with NIR/FTIR detectors. For distinguishing between aviation gasoline (avgas) and jet fuel AVTUR or AVCAT, IR absorptions at 5000–4800, 4000–4500 (or 4000–4400), 2850–2980, 1130–80, 970–1040 and 680–780 (700–800) $cm^{-1}$ may be used, in both cases the Avgas giving the higher absorptions. Absorptions due to isopentane may specifically be sought to distinguish between Avgas which contains significant amounts of isopentane and jet fuel which does not. In the case of UV fluorescence spectroscopy, radiation at a specific wavelength or wavelengths, e.g. 254, 313, 366, 546 nm may be used to excite fluorescence in the visible region, which is detected. Filters at e.g. 370, 420, 450 and/or 550 nm may also be used.

For use with micro-gas chromatography, the vapours can contact the micro-gas chromatography solid state sensor, e.g. a spiral column etched on a silica/glass wafer, which separates them, and then by means of a suitable detector e.g. an optical diode or polymer coated electrochemical detector e.g. polymer coated Group VIII metal such as Pt, determine the amounts of each component and an indication of its nature. The signals from the latter can be analyzed to determine the total amounts and, if on the "correct" side with respect to the threshold or otherwise within the tolerances, then the processor can instruct the controller to open the valve allowing flow to occur when required.

The detector can also be a solid state gas sensor, which is a device whose conductivity is changed in the presence of a gas. Further details of such sensors are described in Sensors and Actuators B Vol.8 1992 pp 1–11 by H V Schurmer et al the content of which is herein included by reference. The detector comprises a sensor for the vapour which may be gas permeable, a support e.g. a membrane therefor, a pair of electrodes on either side of the sensor, e.g. having a reference and sensing electrode, means for providing a voltage across the electrodes and means for detecting any change in the conductance of the sensor e.g. a voltmeter or ammeter. The device is used in association with a data processor to process the output from the sensor. The changes may be in the sensor itself or in a device in contact with the sensor (a pellister approach), such as in relation to a ion sensitive/ selective layer on an electrically conducting-wire or plate or quartz oscillator with a layer of organic sensor adsorbed thereon; swelling of the polymer causes changes in the oscillation frequency of the quartz oscillator, as in a quartz microbalance. Alternatively the quartz layer in the microbalance may be sensitive to the vapour or may be provided with an optionally organic coated metal layer sensitive to the vapour. Thus the quartz layer may have a coating of Group VIII or IB metal such as copper, nickel, gold or ruthenium, platinum, palladium or rhodium. The metal layer may have had an organic coating e.g. of an organic sulphur compound such as an aliphatic aromatic or araliphatic polar compound e.g. thiol such as one with 4–24 carbons such as 6–16 carbons, e.g. dodecylmercaptan, especially on gold, or an aliphatic N-heterocyclic polar compound e.g. imidazoline with 6–24 carbons in the aliphatic e.g. alkyl or alkenyl group such as oleyl imidazoline. The polar organic treated metal may be more sensitive to one fuel over another e.g. kerosene over avgas, while the untreated metal may have a reverse sensitivity. There may be one sensor per device, or an array of sensors e.g. 2–50, 20–40, 2–20 or 3–6 each sensitive to a different compound, thereby enable a "fingerprint" of the vapour to be obtained. While each sensor, or array, may have an associated processor and controller, if desired there may be a number of sensors, but only one processor and controller, the signals from the sensors being scanned and passed to the processor and controller e.g. via a multiplexer. There may be at least one processor per controller usually 1–3, preferably 1, except when a processor is present to provide compensation e.g. for temperature differences between an analysis zone and a standard or another analysis zone.

Solid state sensors e.g. polymer coated metal oxide sensors are commercially available and vary from ones with only one sensor, sold for analysis of and sensitive to gaseous 1–4 carbon alkanes, carbon monoxide or oxygen, or multimatrix ones with many different heads, each sensitive to a different material. It has been found that polymer coated metal oxide sensors sensitive to carbon monoxide and/or methane are sensitive to Avgas and jet fuel as well.

The sensor itself may be inorganic or organic, examples of the former being metal oxide semi conductors, metal oxides SFETS and electrochemical cells, and examples of the latter being conducting polymers, lipid coated wires and Acoustic Wave sensors e.g. operating at 50–500 $MH_z$ e.g. 200–300 $MH_z$. Metal oxide semi conductors are usually based on zinc, tin or titanium oxides with a catalytic metal or rare earth metal associated with them e.g. impregnated thereon, for example platinum or palladium gates. Examples are zinc oxide single crystals with suitable metal; these are also known as Taguchi gas sensors. These work by interaction of the hydrocarbon vapour with air over the catalyst to cause changes in the semi conductivity of the oxide; this interaction happens when the catalyst is heated e.g. to 300–400° C. by a thin film heater, which is adjacent the sensor, usually on the side distant from the vapour source. By using different catalyst metals and/or different temperatures, different sensors interact with different hydrocarbons to different extents. The act of removal of the fuel nozzle from its stand, which usually starts the fuel pump, can trigger heating the heater or powering the sensor. The metal oxide can be on a support e.g. an oxidized silicon wafer or on porous alumina. These metal oxide gas sensors are preferred for sensing the more volatile hydrocarbons e.g. gasoline over diesel and aviation gasoline over jet fuel.

The conductive polymers may be for example optionally substituted poly pyrroles with a variety of cations e.g. sodium, potassium or lithium, and optionally with pendant functional groups. The hydrocarbon vapours may cause the conductive polymer to swell and/or change its permeability to hydrocarbon vapours and/or interact with the conductive polymer to different extents e.g. with formation of ion pairs thereby changing the conductivity of the polymer e.g. polypyrrole to different extents. The polymers may be used as such as the sensor but are preferably supported on a porous support e.g. alumina, or on a membrane, in which case the membrane itself is also externally protected except for a small area for direct exposure to the vapours.

The output signal from the sensor may be a single one for comparison as explained, with the baseline or threshold or another measured signal. The signals from an array may be used to produce a pattern and then the analysed by chemometric techniques for comparison with known patterns e.g. for gasoline or diesel and a decision on the similarity to the known pattern used to control the valve movement. Preferably a single sensor is used to give information so control is based simply on the total vapour concentration especially when the device is for filling tanks with a more volatile fuel e.g. avgas and stopping filling with a less volatile fuel e.g. kerosene. When the sensor is used to differentiate between vapours of 2 different materials, preferably at least two are used, one or more of higher sensitivity to one material and the other or others being of higher sensitivity to the other material. Sensing of one material being the "correct" one, would then require a positive signal from one sensor to which it is more sensitive and a negative signal from the less sensitive sensor. This arrangement significantly increases the safety margin for the device. Another way to increase the margin is to have a reserve sensor in place in case of problems with the main one.

BRIEF DESCRIPTION OF THE DRAWINGS

The invention is illustrated in the enclosed drawings in which.

DETAILED DESCRIPTION OF PREFERRED EMBODIMENTS

Figure 1:
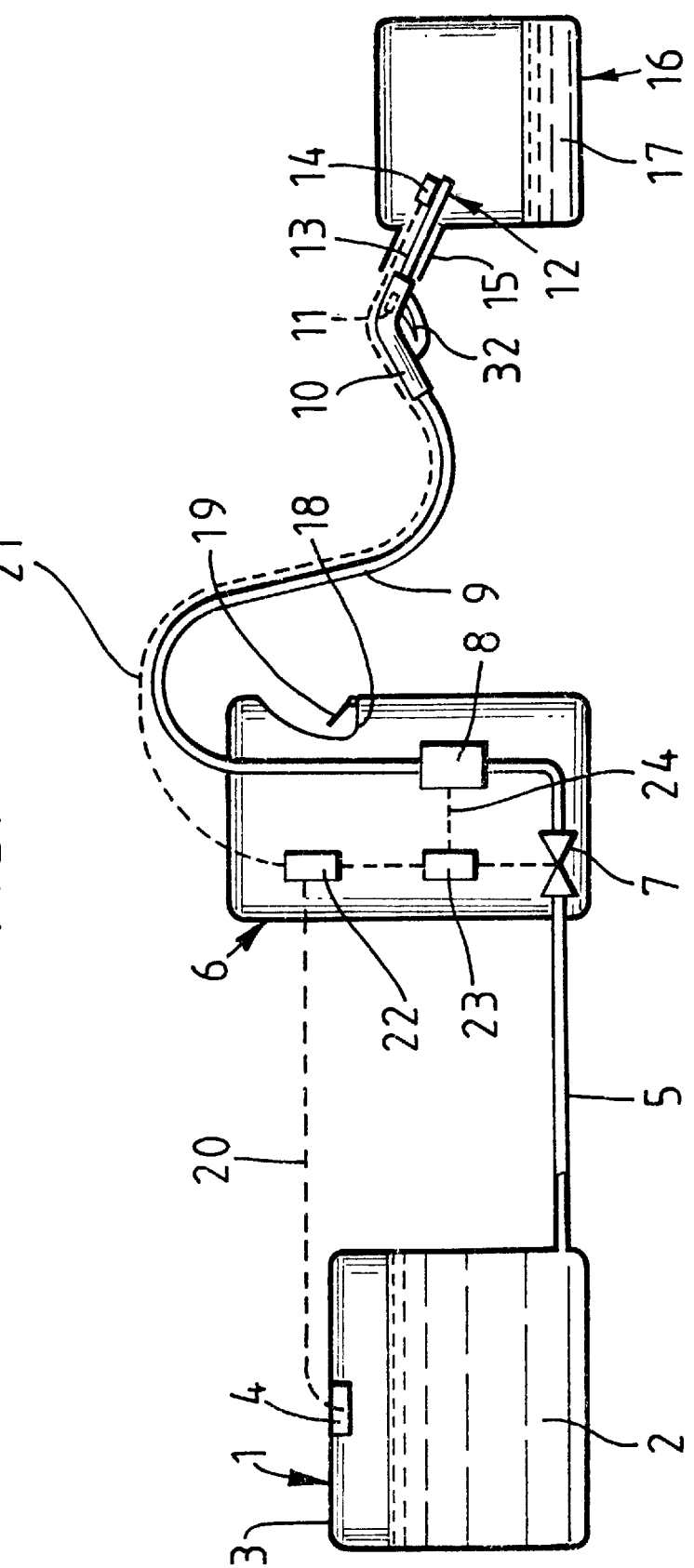
FIG. 1 represents a schematic diagram of the overall apparatus.

Referring now to FIG. 1, a tank 1 containing liquid hydrocarbon 2 has a top surface 3 in which is a first detector 4. From tank 1 leads a first line 5 to a pump stand housing 6 e.g. as in a gasoline filling station. In stand housing 6 on line 5 is a pump 8 and a valve 7 movable between open and closed positions. If desired the pump 8 may also act as a valve instead of separate valve 7. From pump 8 leads a second line 9, usually in part flexible leading to a fuel dispenser or bowser 10, which comprises a manually controlled arm 32 and valve 11 and a projecting nozzle 12. On the upper outside surface 13 of the end of the nozzle 12 is a second detector 14 located in a protective housing (see FIG. 2 for further detail). The nozzle 12 is shown inserted with the neck 15 of the fuel tank 16 of a vehicle e.g. a car, which contains some liquid hydrocarbon 17, above which is vapour, so that the detector 14 is in the vapour.

First (20) and second (21) signal lines lead respectively from the first (4) and second (14) detectors back to the pumpstand housing 6 to a processor 22 which links with a controller 23 in the housing, itself linked via line 24 to control operation of the valve 7 or pump 8. Also shown is the receiving ledge 18 in housing 6 for dispenser 10, which when not in use depresses an arm 19. Alternatively instead of signal lines 20 and 21, the detectors may incorporate electromagnetic radiation generators and the processor 22 corresponding receivers.

When not in use, the dispenser 10 is received in ledge 18 thereby depressing arm 19. For use the dispenser 10 is removed from its ledge 18, releasing arm 19, which turns the power onto the pump 8 and/or can turn power onto the detector 14 or open an optical shutter. The nozzle 12 of the dispenser 10 is then inserted into the neck 15 of the fuel tank 16 of the vehicle. The second detector 14, activated by the power takes a measurement on the vapour in the tank 16, and sends a corresponding signal down line 21 to the processor 22, which compares it with the set threshold. If the signal meets the desired requirements so the vapour is acceptable, then processor 22 instructs controller 23 to open valve 7 or to start pump 8. Alternatively, (not shown) the release of arm 19 would not provide power to the pump 8, until the controller 23 instructed this, based on the instruction from the processor 22; in this case valve 7 may be omitted. Once the valve 7 or pump 8 are open and operating, then lines 5 and 9 are open so that on depression of the manual arm 32 in the dispenser 10 fuel is pumped from tank 1 through pump 8, dispenser 10, nozzle 12 and into tank 16. Once the manual arm 11 is released the flow stops, and the dispenser 10 is returned to its ledge 18 thereby depressing arm 19 and shutting off the pump 8, closing valve 7 (if present) and optionally turning off power to detector 14. The act of return to ledge 18 may trigger an inductive current to recharge the battery in the sensor.

In a modification of the above process, the decision to activate the valve 7/pump 8 is derived from a comparison of the signal from detector 14 in tank 16 with signal from detector 4 in tank 1, which is passed via signal line 20 to processor 22. If the signals have comparable amplitude (within given tolerances e.g. ±10% of the signal), then the processor 22 will instruct the valve 7/pump 8 to open.

In either case if the vapour in tank 16 is different, so that the signal does not reach the threshold (e.g. when tank 1 contains gasoline and tank 16 diesel) or exceeds it (e.g. when the reverse is true), then the processor will reject the signals, and will not instruct the controller 23 to open the valve 7/pump 8. No liquid can then flow from tank 1 to tank 16, thereby obviating a potentially dangerous mis-fueling.

Figure 2:
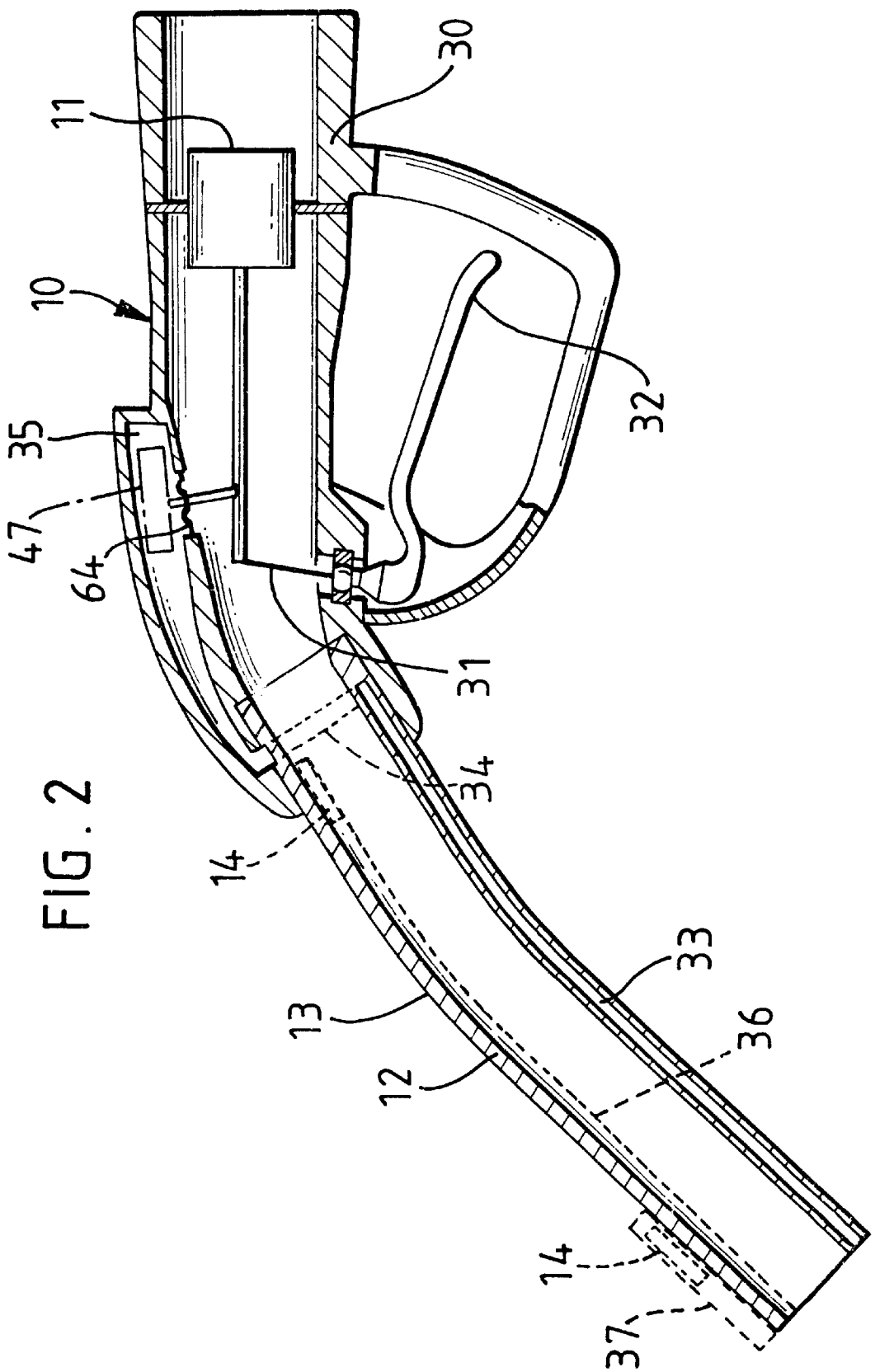
FIGS. 2–8 represent partly schematic drawings partly in section of fuel dispensing nozzles of the invention.

Referring now to FIG. 2, which is a schematic partial cross section through a dispenser of this invention, the dispenser 10 has a nozzle 12 and a body part 30, in which is the control valve 11 held closed by urging means, not shown, but openable by mechanism 31 and manually depressable arm 32. Inside, and integral with or separate inside the nozzle 12 is an overflow cut out conduit 33, extending axially the length of the nozzle and then passing in a tube 34 across the fuel flow inside the body part 30 into a safety housing 35, which contains safety device 47 to shut off flow if the nozzle is tilted sideways and to shut off flow because of an induced vacuum in the conduit following entry of fuel into the conduit 33 due to overflow or frothing in the neck 15. Safety devices 47 comprise a diaphragm (64 see FIG. 4) restrained from movement but whose movement when activated urges a rod to trip a spring loaded arm which closes valve 11, such safety devices are well known in the art and are shown schematically in outline in FIG. 2. The detector 14 may be in the safety housing 35, the insertion of the nozzle 12 into the tank diffusing vapour from the tank up the safety conduit 33 and to the detector 14. Alternatively the detector may be located in the conduit 33 itself or in the nozzle in a separate conduit closed at its top end (36 shown dotted in FIG. 2), or on the outside of the nozzle 12, e.g. on its upper surface 13 in a protective housing 37 (shown dotted in FIG. 2). In each case of location of the detector 14, a signal line 21 and if required power lines (not shown) lead to the processor 22, in the pump housing 6, or, not shown, within the body part 30 or safety housing 35. In the latter cases, the controller 23 is also present in the body part 30 or housing 35, and similarly the line controlling opening/closure of the valve 11. If desired the signal lines can be dispensed with and be replaced by electromagnetic radiation transmitters and receivers.

Figure 3:
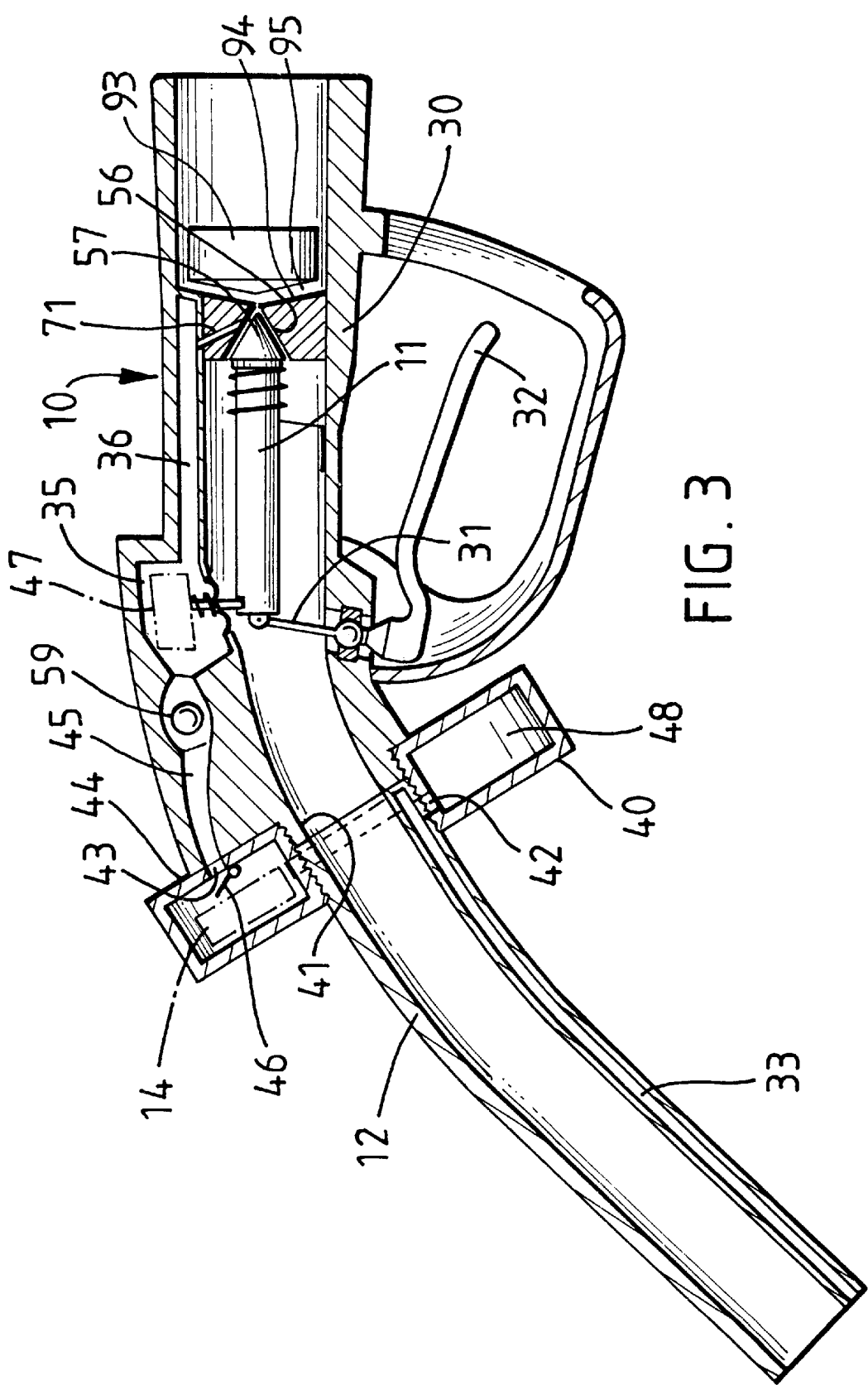

FIG. 3 shows a modification of the dispenser of FIG. 2 in which the nozzle 12 and body 10 of the dispenser are separated by an annular collar 40, whose central core is threaded either to engage with corresponding threads on nozzle 12, which may be of different dimensions for different fuels, and/or a tube 41 extending from body part 30. Collar 40 has an annulus 48 which is open via passage 42 to the threaded portion of nozzle 12 to overflow cut out conduit 33, which leads to outlet 71 in the body part 30 and is open for insertion in the neck 15 of tank 16. The annulus 48 is also open via passage way 43 through the transverse wall 44 of the collar 40 to an elongate channel 45 through the upper surface of body part 30. In channel 45 lies a ball 59 capable of free movement therein but capable of blocking the device 47 end of channel 45. In annulus 48 is located detector 14 with associated processor 22 (not shown) and controller 23 (not shown), and signal or radiation transmitters/receivers (not shown), as well as a valve 46 or other closure device activatable by controller 23 to move between open and closed positions across passageway 43. Valve 46 may be replaced by any means for creating a pressure difference in passageway 43. Valve 11 has a nose 57 located in a seating surface 56, into which leads a thin channel 71 passing into a longitudinal passageway 36 leading to housing 35. Passage of fuel past seating surface 56 causes suction in channel 71 and hence to conduit 33. Upstream of nose 57 in the line of liquid inlet flow through body 10 is a flow controller 93 with a downstream conical face defining with a seating 94 a conical annular fluid channel 95.

In use of the dispenser of FIG. 3, insertion of nozzle 12 into the neck of the fuel tank 16 forces vapour from above the tank 16 up conduit 33, and via passage 42 into annulus 48 where it contacts detector 14, which passes a signal to processor 22. If the processor 22 confirms that the vapour is of the correct fuel, then it passes a signal to controller 23 to open flap or valve 46 (or maintain flap open), thereby allowing vapour to reach the safety device 47 in its housing 35. Manually squeezing arm 32 moves valve 11 to move away from seating surface 56 allowing fuel to pass through body 30 and out through nozzle 12 and into tank 16. However, if processor 22 finds that the vapour is of the incorrect fuel, then a signal is passed to controller 23 which activates flap or valve 46 to shut it (or keep it shut), thereby stopping air from reaching safety device 47, this stoppage causes a slight suction in elongate channel 45 thereby activating safety device 47 which stops further opening of valve 11. No fuel can then flow.

In the FIGS. 2 and 3 devices, preferably the processor 22 compares the results from detector 14 with an internal standard, preset for the fuel in tank 1. By this means transmission of signals significant distances is avoided, thereby aiding miniaturisation. If desired annulus 48 may have an axial length substantially greater e.g. more than 3 times greater than its transverse width, rather than of substantially similar dimensions.

Detector 14 and associated processor 22 and controller 23 may be sealed in annulus 48, but if desired collar 40 may be in two parts or have an access flap (not shown) to allow their replacement or adjustment.

Figure 4:
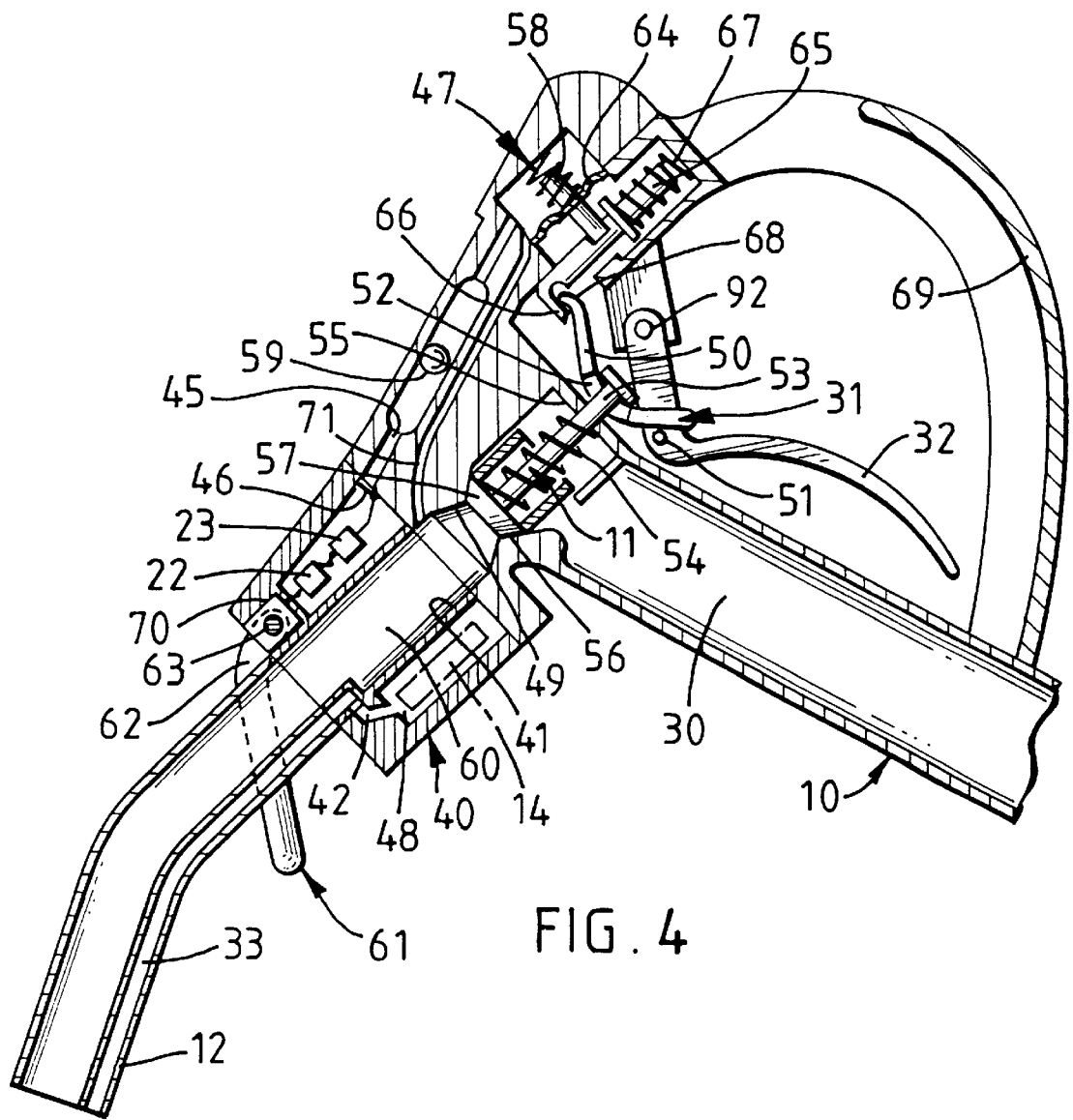

FIG. 4 shows an embodiment of the dispenser of the invention. Body 10 has fuel tube 30 leading to valve 11 and nozzle 12. Arm 32 co-operates with mechanism 31 shown as a bifurcated body 50 and projecting lug 51. Arm 32 is pivotally mounted on body 10 by pin 92. Body 50 has a central slot 52 in which core 53 of valve 11 is free to move. Compression spring 54 constitutes urging means urging core 53 and hence valve 11 away from bearing surface 55 and towards a frusto-conical seating surface 56. Conical nose 57 is at the end of valve 11 distant from surface 55 and sealingly engaged by seating surface 56. Between nozzle 12 and nose 57 lies a neck 49 and a fuel passage 60 defined by walls 41 and passing axially through collar 40., Walls 41 separate passage 60 from an annulus 48 in collar 40. A passage 42 leads from annulus 48 to overflow cut out conduit 33 which leads inside down nozzle 12, to its end. Annulus 48 surrounds passage 60 and contains detector 14, processor 22, controller 23 and to which is electrically attached a generator 70. A depressable arm 61 has two extending legs 62 on either side of nozzle 12. The legs 62 are kept in place on collar 40 with an axle 63 passing through eyelets in each leg, and the arm is urged away from collar 40 by springs (not shown) acting on legs 62. Surrounding axle 63 is the generator 70. A flap or valve 46 is located at the exit from annulus 48 towards a safety passage 45 in the upper part of body 10 leading to a safety device 47. Safety device 47 comprises a spring loaded diaphragm 64 having a core 58 the distant end of which is located in a bar 65 which it restrains from movement. Bar 65 carries a lower ledge 66. One end of body 50 has a lip 68, which bears on ledge 66. Rod 65 is urged forwards towards nozzle 12 by spring 67. Handle 69 extends between safety device 47 and body 10. In safety passage 45 is a ball 59 free to move in a broadened section of passage 45 and able to allow air to move past the ball 59 except when the ball is at the end of the broadened section near to device 47. A thin channel 71 extends between neck 49 and device 47.

In use nozzle 12 is inserted into the neck of a tank containing liquid and residual vapour of a fuel; the insertion is such that arm 61 is depressed rapidly thereby causing generator 70 to produce electricity to power detector 14, processor 22, and controller 23 which are joined by wire lines. If desired not shown, generator 70 may be omitted, the power coming from an alternative source e.g. a battery and the depression of the arm 61 simply operating a switch allowing the power to activate the detector etc. The act of insertion is also such as to direct vapour of the fuel along conduit 33 and into chamber 48 and also to ensure that the nozzle is inserted to a constant distance into the neck of the tank each time and hence to a similar vapour concentration. Detector 14 detects the vapour and passes a signal to processor 22 which determines, by reference to standards or otherwise, whether the fuel is the correct fuel, and instructs controller 23 to open or close flap or valve 46. If flap or valve 46 is closed, the passage of any fuel past neck 49 creates suction in tube 71 which triggers diaphragm 64 to move inwardly withdrawing core 58 and releasing rod 65, which moves forwards thereby causing lip 68 of bifurcated body 50 to move and allow valve 11 to be shut; no fuel can flow. If the "correct" fuel is sensed, pulling of arm 32 towards handle 69 causes lip 51 to bear on arm 31 which with ledge 66 on lip 68 pulls valve core 53 and hence opens valve 11 allowing fuel to flow.

Figure 5:
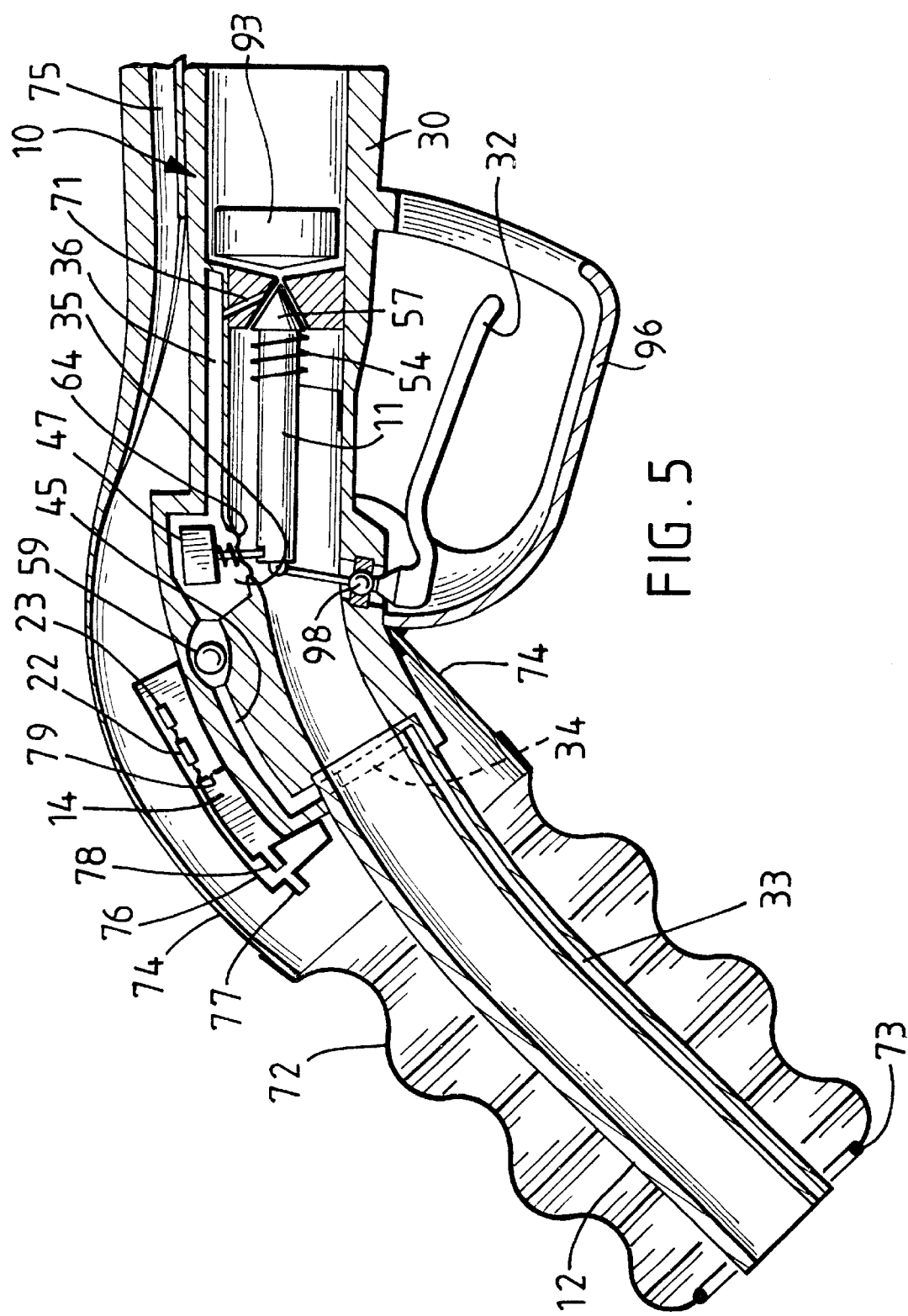

FIG. 5 shows a modification of the dispenser of FIG. 3. Components comparable to those in FIGS. 1–4 have been numbered the same and their location and role are not further described unless necessary. The dispenser of FIG. 5 has surrounding nozzle 12 a skirt 72 which is flexible and collapsible having at its lower end a weighted ring (or sections of ring) 73 and at its upper end is attached to a rigid hollow frame 74 which surrounds the upper end of the nozzle and the head end of the body 30 of the dispenser up to a guard 96 for arm 32; the hollow frame 74 also extends over the top of body 30, where it becomes a rigid body with a vapour recovery conduit 75. Between nozzle 12 and safety device 47 on the top of body 30 in the region, where safety passage 45 is located, is mounted (by means not shown) a detection and control housing 76 which contains sensor 14 processor 22 and controller 23, joined by wires. Housing 76 is provided with a forward facing entry port 77, while sensor 14 has entry 78 and exit 79 orifices. Arm 32 is mounted on pivot 98 to act to pull valve 11.

In use the vapour recovery system e.g. operated from the pump 8 region pulls vapour into conduit 75 from skirt 72 and past housing 76. When the nozzle 12 is inserted in the tank of the vehicle to be fuelled, the skirt 72 collapses and vapour from the tank is drawn up past housing 76. Some vapour enters through port 77 and orifice 78 to sensor 14 where it is analyzed and the results passed to processor 22 and controller 23. Controller 23 can transmit a signal by radio or fibre optic cable (not shown) (e.g. along conduit 75) to instruct the pump 8. Alternatively controller 23 can act on ball 59 causing it to move; thus ball 59 may be of metal and the part of the body 30 above the ball may be of plastics material, so that an induced magnetic field from controller 23 can move ball 59 from a position from open to closure of channel 45. By the above means, if the sensor 14 detects the "correct" fuel vapour, fuel will flow continuously on depression of arm 32. If the sensor 14 detects the wrong vapour, controller 23 will cause the pump 8 to stop or channel 45 to block thereby creating suction in housing 35 and causing diaphragm 64 to move inwardly releasing valve 11 which closes; no fuel can flow.

Figure 6:
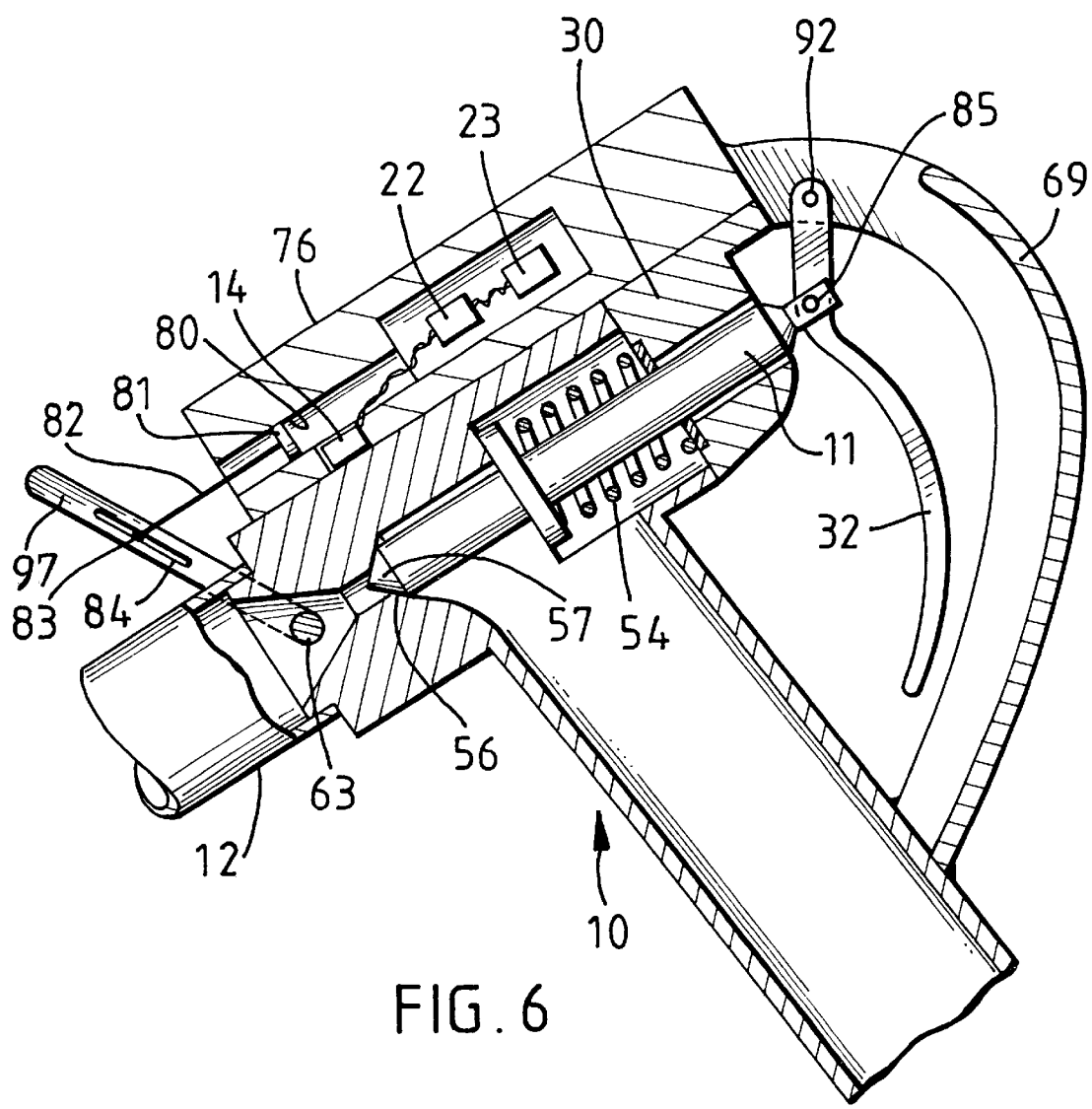

FIG. 6 is a modification of the dispenser of FIG. 4 of the invention, again like parts to those in FIGS. 1–5 having like numbering. FIG. 6 differs from FIG. 4 in having no safety device 47 and its assorted related components and no annular chamber 40 for the sensor etc. However, FIG. 6 shows a detection control housing 76 mounted (by means not shown) on the body 30. Inside housing 76 are sensor 14, processor 22 and controller 23 jointed by wires. Sensor 14 is located off a shaft 80 in which moves a piston 81 under the influence of rod 82 and urged by movement of arm 97 against a return spring (not shown). A pivot 83 moves in arm 61 in an axial slot 84. Nose 57 of valve 11 is urged towards seating surface 56 by spring 54 while valve 11 is pivoted by pin 85 on arm 32.

In use of FIG. 6 insertion of nozzle 12 into the tank depresses arm 61 causing piston 81 to move along shaft 80 past sensor 14, thereby drawing vapour from the tank onto sensor 14, which passes a signal to processor 22 and hence controller 23. If the signal shows an accepted fuel, pump 8 can operate so raising of arm 32 withdraws valve 11 and fuel flows down nozzle 12. If the fuel is "incorrect" controller 23 signals by radio or fibre optic link to the pump controller to block operation of the pump, so no fuel can flow.

Figure 7:
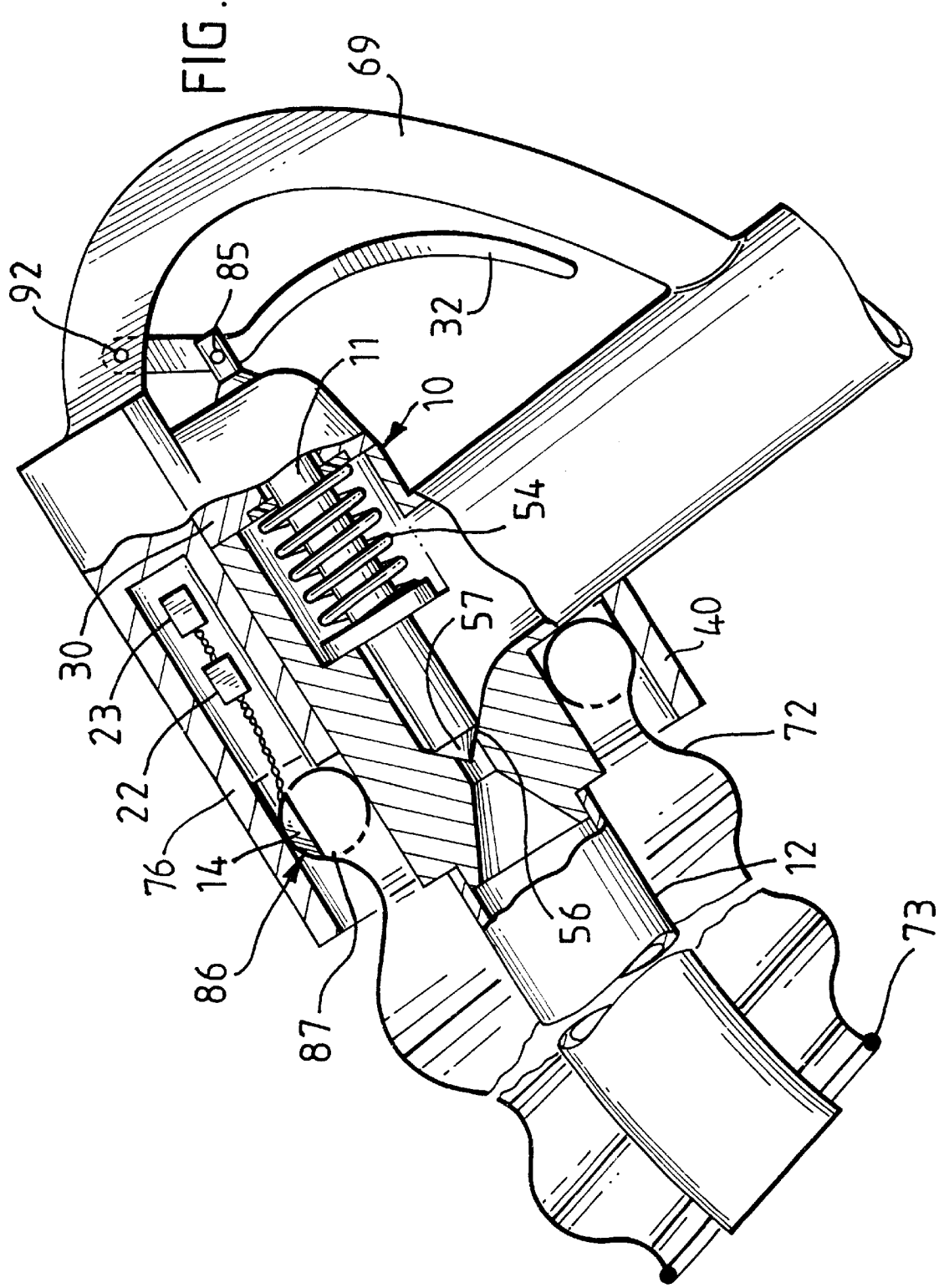

FIG. 7 is a modification still of FIG. 6, there is no depressable arm 61 or piston to suck the vapour past the sensor 14. However the FIG. 7 shows a skirt 72 around the nozzle as in FIG. 5, and a toroidal collar 86 containing the sensor 14. The collar 86 has an internally reflecting surface and perforations 87 downwardly facing towards nozzle 12. Sensor 14 is joined to processor 22 by a wire. In use insertion of nozzle 12 into the tank collapses skirt 72 driving vapour upwards towards the perforations 87 and into the collar 86, where it is analyzed by sensor 14, the results passed to processor 22 and hence controller 23, from whence a signal is sent by radio or fibre optics to the pump, with subsequent operation or not as in FIG. 6.

Figure 8:
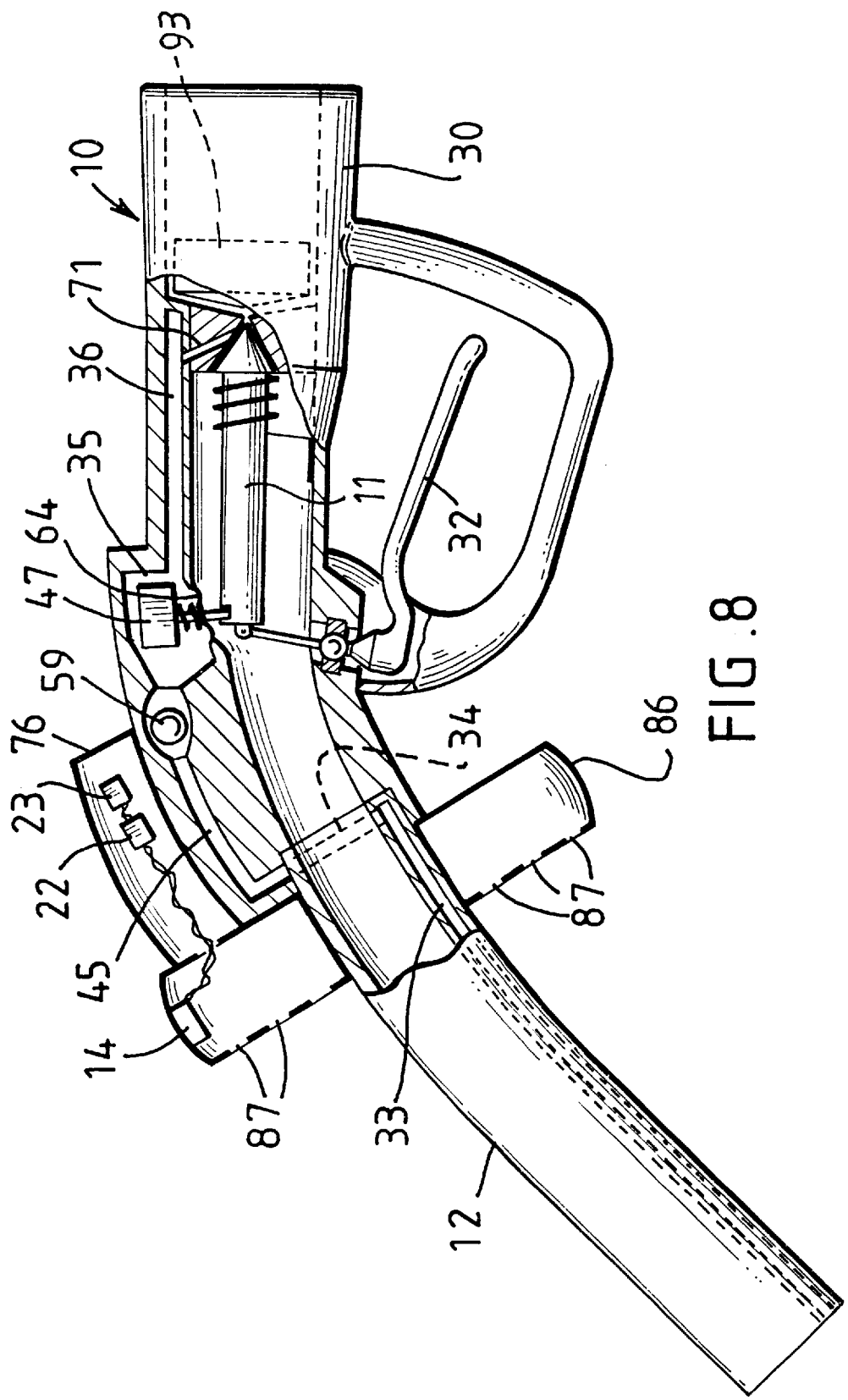

FIG. 8 show a modification of the dispensers of FIG. 3 and 5, but has no skirt, and the sensor 14 is in a different location. Surrounding the part of nozzle 12 nearest the head portion of body 30 is a toroidal collar 86 internally metallized and having downwardly facing perforations 87 towards the nozzle. Sensor 14 is inside collar 86 and signals from it pass by wire to processor 22 and controller 23. The conduit 33 is open via tube 34 to passage 45 and housing 35 and hence to thin tube 71, so in use the automatic cut operation represented by these features operates conventionally. The difference lies in the presence of collar 86 and housing 76 which can be retrofitted to an existing dispenser. Vapours from the tank enter the collar 86 by way of perforations 87, are sensed by sensor 14 and the results passed through to controller 23 as in the other Figures. Controller 23 can cause ball 59 to close the passage 45 or can signal to the pump.

EXAMPLES

This invention will now be further described with reference to the following examples.

Example 1

Samples of each of a Jet Fuel, which was DEF-STAN 91-91, NATO Code F35, Jet A1-AVTUR, and an Avgas, which was Aviation Gasoline 100LL/DEF-STAN 91-90, were poured into cans to half fill them with liquid, the remaining space being filled with vapour. An aspirator pipe was inserted into each vapour, and the gases which were aspirated, were passed into a 10 cm gas infra red spectrometer cell, where the spectrum of each was recorded. The results were as follows, with the main absorption regions being quoted.

| Wavenumbers $cm^{-1}$/Absorbances (times 1000) | | | | | | | |
|---|---|---|---|---|---|---|---|
| 5000 | 4800 | 4600 | 4440 | 4400 | 4350 | 4320 | 4270 |
| Jet 2.5 | 2.6 | 2.8 | 2.9 | 3.1 | 3.5 | 3.5 | 3.5 |
| Avgas 4.75 | 4.35 | 4.0 | 4.0 | 5.0 | 5.25 | 5.25 | 4.8 |

Thus analysis of an unknown at 5000–4800 or 4400–4270 especially 4390–4410, 4320–4350 or 4250–4300 especially 4270–8 $cm^{-1}$ shows from the size of the absorbance whether the unknown is avgas or jet fuel.

In the IR region of 3100–2800 $cm^{-1}$, the results were as follows.

| Wavenumbers $cm^{-1}$/Absorbances | | | | | | | |
|---|---|---|---|---|---|---|---|
| 2980 | 2950 | 2940 | 2930 | 2920 | 2900 | 2880 | 2860 |
| Jet 0.96 | 1.56 | 1.88 | 2.24 | 1.48 | 0.76 | 1.00 | 0.88 |
| Avgas 1.28 | 1.16 | 0.90 | 0.76 | 0.70 | 0.60 | 0.64 | 0.24 |

Thus analysis of an unknown at 2930–40, or 2860–2880 $cm^{-1}$ shows whether the unknown is jet fuel or avgas.

In the IR region of 1300–900 $cm^{-1}$, the results were as follows.

| Wavenumbers $cm^{-1}$/Absorbances (Times 1000) | | | | | | | | |
|---|---|---|---|---|---|---|---|---|
| 1200 | 1175 | 1160 | 1150 | 1135 | 1035 | 1025 | 975 | 970 |
| Jet −4 | −1 | 0 | 0 | −1 | −1 | −1 | 0 | 0 |
| Avgas 0 | 10 | 16 | 15 | 11 | 6.5 | 11 | 17.5 | 7.5 |

Thus analysis of the unknown at 1130–1180 especially 1140–1175, or 970–1040 e.g. 1025 or 975 $cm^{-1}$ shows whether the unknown is jet fuel or avgas.

The differences in absorption can thus be used to control a pump feeding jet fuel into aircraft by sampling the vapour in the aircraft fuel lines (via an aspirated suction line to the spectrometer), noting the size of the absorption at one of those absorptions detailed above and controlling activation of the pump or opening of a valve allowing fuel to pass into the aircraft fuel lines and hence tank depending on whether the absorption is above or below an appropriate value at that wavenumber. Thus in the above tests, with absorptions above 0.0035 at 4400–5000 $cm^{-1}$ or 0.0042 at 4250 to 4450 $cm^{-1}$ or 0.005 at 1125–1180 $cm^{-1}$ or 0.004 at 970–1040 $cm^{-1}$ a pump feeding jet fuel would be stopped, while a reading above 1.2 at 2920–2940 $cm^{-1}$ would activate the pump or open the valve allowing jet fuel into the fuel lines and tank. In practical operation, the instruments would be calibrated before use.

Example 2

The samples of liquid and vapour for the Avgas and Jet Fuel of Ex. 1 and also for another jet fuel, diesel oil and motor gasoline, were prepared as in Ex. 1, and the vapours aspirated past a commercially available electronic gas sensor GMI Gas Surveyor 412 electronic sensor, sensitive to the detection of methane in air (from Gas Measurements Instruments, Renfrew Scotland); the sensor had a polymer coating on a metal oxide base, and had been sold for detecting hydrocarbons of 1–4 carbons, carbon monoxide and oxygen. The vapours were tested 2 mm into the necks of the cans.

The readings for the vapours of jet fuel (whether AVTUR or AVCAT) and avgas were <1 and >100 respectively while those for the vapours of diesel oil and motor gasoline were <1 and >100 respectively.

In the same way as in Example 1, the sensor can be used to control a pump feeding jet fuel to an aircraft fuel tank, by sampling the vapour in the tank or in the tank neck as above and controlling the pump depending on whether the reading is above or below a specific reading, in this specific test 40–70, i.e. activating the pump or opening the valve if the reading is below 40–70 corresponding to jet fuel in the tank. Likewise if measurement is made in the tank or tank neck and jet fuel would be fed by the pump and the reading is above 40–70, then the tank clearly contains avgas and the pump would not be started and/or the valve would be at closed.

Example 3

Samples of vapours from jet fuel and avgas were kept in separate containers, and the vapours aspirated past a multi-matrix polymer coated metal oxide sensors A32S, commercially available from AROMASCAN plc, Crewe, England. The sensor has different polymer coatings in the 32 matrix heads. The results were analysed by Neural Analysis in a 5 point scan. The results were expressed on a 2-dimensional Principle Components Analysis Graph, which showed that the weighted average of the 5 results from each kind of vapour differed significantly, the average value of (PCA1) along the abcissa (x axis) for the avgas being significantly larger than that for jet fuel. Thus the sensors can be used in the same way as in Ex. 2.

Example 4

The method of Ex. 2 was repeated with the vapours tested 2 cm above the can mouth and also in the vapour in the cans. The results were as follows.

|  | Readings | |
| --- | --- | --- |
|  | Above Can mouth | In Can |
| Jet Fuel | 1 | 11 |
| Avgas | 16 | >100 |

Example 5

The method of Ex. 1 was repeated with a stream of dry nitrogen blown over the fuel in a container and into the IR gas cell. The spectral results at 4000–4500 $cm^{-1}$ were as follows.

| | Wavenumbers $cm^{-1}$/Absorbance (x 1000) | | | | | |
| --- | --- | --- | --- | --- | --- | --- |
| | 4050 | 4100 | 4200 | 4300 | 4350 | 4400 |
| Jet | 0 | 0 | 0 | 0 | 0 | 0 |
| Avgas | 4 | 5 | 3.6 | 6 | 8.4 | 6 |

Thus measurement at 4050–4450 $cm^{-1}$ differentiates between avgas and jet fuel. The results at 700–800 $cm^{-1}$ were as follows:

| | Wavenumbers $cm^{-1}$/Absorbances | | | |
| --- | --- | --- | --- | --- |
| | 700 | 730 | 740 | 750 |
| Jet | 0.16 | 0.4 | 0.2 | 0.1 |
| Avgas | 0 | 0.04 | 0 | 0 |

Measurement at 700–750 $cm^{-1}$ differentiates between avgas and jet fuel, the latter giving the higher absorptions.

The spectral differences between the avgas and jet fuel can be used to control the flow of fuel as described in Ex. 1.

Example 6

The method of Ex. 1 was repeated with vapours from diesel fuel and motor gasoline, (Mogas), in this case unleaded gasoline of MON 84.6 and RON 96.2. The absorptions in the 4500–4000 $cm^{-1}$ region were as follows:

| | Wavenumbers $cm^{-1}$/Absorbances x $10^3$ | | | | |
| --- | --- | --- | --- | --- | --- |
| | 4430 | 4400 | 4300 | 4250 | 4040 |
| Mogas | 30 | 48 | 52 | 45 | 30 |
| Diesel | 7 | 7 | 8 | 8 | 6 |

Hence absorptions in the region 4040–4420 $cm^{-1}$ differentiate between the mogas and diesel.

The results in the 600–80 $cm^{-1}$ region were as follows:

| | Wavenumbers $cm^{-1}$/Absorbance | | | |
| --- | --- | --- | --- | --- |
| | 770 | 750 | 725 | 700 |
| Mogas | 0 | 0 | 0.04 | 0 |
| Diesel | 0.1 | 0.1 | 0.4 | 0.16 |

Absorptions at 680–770 $cm^{-1}$ differentiate.

In the field e.g. on a gasoline filling station or airport filling point, the spectra would be contaminated with absorptions from carbon dioxide and water, whose spectra at 5530–5100, 4000–3350, 2100–1300 and less than 500 $cm^{-1}$ would if required need to be subtracted from the spectra of the fuels.

Example 7

Two quartz crystal microbalances were used, one (A) with a vacuum deposited gold layer on the oscillating quartz crystal and the other (B) with the vacuum deposited gold layer pretreated with organic solution of dodecylmercaptan in toluene for 12 hr followed by evaporation of solvent. Each microbalance had the planar quartz crystal bonded on either side to a conductor, which were joined in an oscillator circuit, set to oscillate at a frequency of 10 MHz. Changes in frequency on immersion of the microbalance into the vapour above 10 ml of fuel in a 20 ml vessel were noted. The fuels were avgas and jet fuel used in the earlier Examples. The results were as follows.

Balance (A). Avgas change 80 Hz, jet fuel change 190 Hz. In a different location for the balance Avgas change 60 Hz, jet fuel change 120 Hz.

Balance (B). Avgas change 400 Hz, jet fuel change 700 Hz. With these balances as detectors mounted on a dispenser nozzle as shown in the accompanying drawings one can control fueling and avoid misfuelling of an aircraft with avgas or jet fuel.

We claim:

1. A method for controlling the movement of a liquid, from a first location to a second location via a dispenser for the liquid located in a liquid line between the first and second location, wherein the dispenser comprises a nozzle, an internal liquid conduit, a valve, a body portion, a hollow annular collar and a first detector and wherein the first detector is located in the collar which is positioned around the nozzle or between the nozzle and the body portion such that the first detector is in vapor communication with a vapor space above the second location, said method comprising analyzing the vapor from said vapor space by withdrawing the vapor past the first detector and using the results of the analysis to control the operation of said valve, wherein the first location has a vapor space above the liquid and a second detector is placed in vapor communication with said vapor space, the method comprising analyzing the vapor in or from the second location and in or from the first location, and comparing the results of the analysis in or from the second location with the results from the analysis in or from the first location.

2. A method according to claim 1 wherein the analysis of the vapor from said vapor space is compared to a standard.

3. A method according to claim 1 wherein the control of the operation of the valve is automatically dependant upon the results of the analysis.

4. A method according to claim 1 wherein the liquid comprises a liquid hydrocarbon.

5. A method according to claim 4, wherein the vapor in each of the first and second locations is independently selected from the group consisting of:

(a) aviation gasoline and kerosene, (b) motor gasoline and diesel oil, and (c) leaded and unleaded gasoline.

6. A method according to claim 1 wherein the analysis is of total vapor concentration and the comparison of the results of the analysis controls operation of the valve depending on whether the total vapor concentration is above or below a defined level.

7. A method according to claim 1 wherein the analysis is specific to at least one compound present in said liquid and the comparison of the results of the analysis controls operation of the valve depending on whether the amount of said compound(s) present is above or below a defined level.

8. A method according to claim 1 wherein the first location is a non-movable tank of liquid and the second location is a tank of a movable vehicle.

9. A method according to claim 1 wherein the annular collar also comprises a processor to analyze the results from the detector and a valve controller to act on instructions from said processor.

10. A method according to claim 1 wherein the annular collar is separate from but in use engageable with the nozzle and/or the body portion of the dispenser.

11. A method according to claim 1 wherein the valve is shut in response to the activation of an alarm.

12. A method as claimed in claim 11 wherein the alarm is an audible and/or optical warning.

13. An apparatus which is a liquid dispenser comprising
a tank containing vapor;
a nozzle for the exit of liquid which nozzle is insertable into said tank containing vapor;
an internal liquid conduit through the dispenser for the liquid;
a valve in said conduit for control of dispensing said liquid;
a body portion;
a hollow annular collar;
a first detector;
a processing means;
a first means for passing a signal from said first detector to said processing means for comparison of said signal; and
a valve controller means;
said detector being located in the collar which is positioned around the nozzle or between the nozzle and the body portion, wherein in use vapors at the exit end of the nozzle are drawn into the collar and past the first detector, wherein said apparatus comprises a second detector adapted to be in vapor communication with vapors at the uptake end of the dispenser and a second means for passing a signal from said second detector to the processing means for comparison with the signal from said first detector.

14. An apparatus according to claim 13 wherein said apparatus comprises a means for passing a signal from said processing means to said controller which receives output from said analysis for controlling the operation of the valve.

15. An apparatus according to claim 13 wherein the processing means and the controller means are located in the collar.

16. An apparatus according to claim 13 wherein said valve is urged to a closed position by urging means but is releasably openable against said urging means.

17. An apparatus according to claim 13 wherein the annular collar is separate from but in use engageable with the nozzle and the body portion of the dispenser.

18. An apparatus according to claim 13 wherein the detector is selected from the group consisting of spectroscopic detectors, gas chromatographic devices and olfactory sensors.

19. An apparatus according to claim 18 wherein the detector is an infra red detector.

20. An apparatus according to claim 13 wherein the detector is battery powered and the batteries are recharged by induction when waiting for use.

21. An apparatus according to claim 13 wherein the controller operates an alarm.

22. An apparatus according to claim 21 wherein the alarm provides an audible and/or optical warning.

23. A method for controlling the movement of a liquid, from a first location to a second location via a dispenser for the liquid located in a liquid line between the first and second location, wherein the dispenser comprises a nozzle, an internal liquid conduit, a valve, a body portion, a hollow annular collar and a first detector and wherein the first detector is located in the collar which is positioned around the nozzle or between the nozzle and the body portion such that the first detector is in vapor communication with a vapor space above the second location, said method comprising analyzing the vapor from said vapor space by withdrawing the vapor past the first detector and using the results of the analysis to control the operation of said valve wherein the annular collar also comprises a processor to analyze the results from the detector and a valve controller to act on instructions from said processor.

24. An apparatus which is a liquid dispenser comprising
a tank containing vapor;
a nozzle for the exit of liquid which nozzle is insertable into said tank containing vapor;
an internal liquid conduit through the dispenser for the liquid;
a valve in said conduit for control of dispensing said liquid;
a body portion;
a hollow annular collar;
a first detector;
a processing means;
a first means for passing a signal from said first detector to said processing means for comparison of said signal; and
a valve controller means;
said detector being located in the collar which is positioned around the nozzle or between the nozzle and the body portion, wherein in use vapors at the exit end of the nozzle are drawn into the collar and past the first detector, wherein the processing means and the controller means are located in the collar.

* * * * *